United States Patent
Thrower et al.

(10) Patent No.: US 8,423,130 B2
(45) Date of Patent: Apr. 16, 2013

(54) OPTIMIZATION OF THRESHOLDS FOR EATING DETECTION

(75) Inventors: James Thrower, Oakland, NJ (US); Paul Goode, Cherry Hill, NJ (US); Shai Policker, Tenafly, NJ (US); Anat Kliger, Tel-Aviv (IL)

(73) Assignee: Metacure Limited, Hamilton (BM)

( * ) Notice: Subject to any disclaimer, the term of this patent is extended or adjusted under 35 U.S.C. 154(b) by 923 days.

(21) Appl. No.: 12/256,819

(22) Filed: Oct. 23, 2008

(65) Prior Publication Data

US 2009/0281449 A1    Nov. 12, 2009

Related U.S. Application Data

(60) Provisional application No. 61/051,901, filed on May 9, 2008.

(51) Int. Cl.
*A61B 5/05* (2006.01)

(52) U.S. Cl.
USPC .......................................................... 600/547

(58) Field of Classification Search .................. 600/546, 600/547, 585, 595, 300; 607/2, 40, 41, 45, 607/58, 62; 708/109; 128/903, 920
See application file for complete search history.

(56) References Cited

U.S. PATENT DOCUMENTS

| | | | |
|---|---|---|---|
| 3,411,507 A | 11/1968 | Wingrove | |
| 4,133,315 A | 1/1979 | Berman et al. | |
| 4,416,267 A | 11/1983 | Garren et al. | |
| 4,592,339 A | 6/1986 | Kuzmak | |
| 4,823,808 A | 4/1989 | Clegg et al. | |
| 4,975,682 A | 12/1990 | Kerr et al. | |
| 5,074,868 A | 12/1991 | Kuzmak | |
| 5,188,104 A | 2/1993 | Wernicke et al. | |
| 5,226,429 A | 7/1993 | Kuzmak | |
| 5,234,454 A | 8/1993 | Bangs | |
| 5,263,480 A | 11/1993 | Wernicke et al. | |

(Continued)

FOREIGN PATENT DOCUMENTS

EP    1 004 330    5/2000
WO    WO 97/25098    7/1997

(Continued)

OTHER PUBLICATIONS

An Office Action dated May 27, 2011, which issued during the prosecution of U.S. Appl. No. 11/573,722.

(Continued)

*Primary Examiner* — Brian Szmal
*Assistant Examiner* — Mehari Kidanemariam
(74) *Attorney, Agent, or Firm* — William H. Dippert; Eckert Seamans Cherin & Mellott, LLC

(57) ABSTRACT

A method is provided that includes providing a fundic impedance signal of a subject sensed during an initial calibration period using at least one implantable fundic sensor of an eating detection device. An indication is received of actual ingestion events of the subject during the initial calibration period. Using a cost function, an analysis is performed of the fundic impedance signal and the actual ingestion events. Responsively to the analysis, a threshold is set, the crossing of which by the fundic impedance signal is indicative of ingestion. The threshold is stored in a memory of the eating detection device. Other embodiments are also described.

28 Claims, 8 Drawing Sheets

U.S. PATENT DOCUMENTS

| | | | |
|---|---|---|---|
| 5,363,103 A * | 11/1994 | Inkol | 342/13 |
| 5,368,028 A | 11/1994 | Palti | |
| 5,423,872 A | 6/1995 | Cigaina | |
| 5,449,368 A | 9/1995 | Kuzmak | |
| 5,540,730 A | 7/1996 | Terry et al. | |
| 5,601,604 A | 2/1997 | Vincent | |
| 5,690,691 A | 11/1997 | Chen et al. | |
| 5,692,501 A | 12/1997 | Minturn | |
| 5,716,385 A | 2/1998 | Mittal et al. | |
| 5,795,304 A | 8/1998 | Sun et al. | |
| 5,836,994 A | 11/1998 | Bourgeois | |
| 5,861,014 A | 1/1999 | Familoni | |
| 5,868,141 A | 2/1999 | Ellias | |
| 5,891,185 A | 4/1999 | Freed et al. | |
| 5,938,669 A | 8/1999 | Klaiber et al. | |
| 5,979,449 A | 11/1999 | Steer | |
| 5,995,872 A | 11/1999 | Bourgeois | |
| 6,026,326 A | 2/2000 | Bardy | |
| 6,067,991 A | 5/2000 | Forsell | |
| 6,091,992 A | 7/2000 | Bourgeois | |
| 6,104,955 A | 8/2000 | Bourgeois | |
| 6,129,685 A | 10/2000 | Howard | |
| 6,135,978 A | 10/2000 | Houben et al. | |
| 6,185,452 B1 | 2/2001 | Schulman et al. | |
| 6,453,907 B1 | 9/2002 | Forsell | |
| 6,454,699 B1 | 9/2002 | Forsell | |
| 6,460,543 B1 | 10/2002 | Forsell | |
| 6,516,227 B1 | 2/2003 | Meadows et al. | |
| 6,571,127 B1 | 5/2003 | Ben-Haim et al. | |
| 6,600,953 B2 | 7/2003 | Flesler et al. | |
| 6,735,477 B2 | 5/2004 | Levine | |
| 6,832,114 B1 | 12/2004 | Whitehurst et al. | |
| 7,006,871 B1 | 2/2006 | Darvish et al. | |
| 7,009,511 B2 | 3/2006 | Mazar et al. | |
| 7,343,201 B2 | 3/2008 | Mintev | |
| 7,502,649 B2 * | 3/2009 | Ben-Haim et al. | 607/40 |
| 7,775,993 B2 * | 8/2010 | Heruth et al. | 600/587 |
| 2001/0011543 A1 | 8/2001 | Forsell | |
| 2002/0026141 A1 | 2/2002 | Houben et al. | |
| 2002/0103424 A1 | 8/2002 | Swoyer et al. | |
| 2002/0161414 A1 | 10/2002 | Flesler et al. | |
| 2002/0165589 A1 | 11/2002 | Imran et al. | |
| 2003/0009202 A1 | 1/2003 | Levin | |
| 2003/0055464 A1 | 3/2003 | Darvish et al. | |
| 2003/0055467 A1 | 3/2003 | Ben-Haim et al. | |
| 2003/0066536 A1 | 4/2003 | Forsell | |
| 2003/0114899 A1 | 6/2003 | Woods et al. | |
| 2003/0144708 A1 | 7/2003 | Starkebaum | |
| 2003/0208242 A1 | 11/2003 | Harel et al. | |
| 2004/0044376 A1 | 3/2004 | Flesler et al. | |
| 2004/0059393 A1 | 3/2004 | Policker et al. | |
| 2004/0098068 A1 | 5/2004 | Carbunaru et al. | |
| 2004/0106963 A1 | 6/2004 | Tsukamoto et al. | |
| 2004/0147816 A1 * | 7/2004 | Policker et al. | 600/300 |
| 2004/0249421 A1 | 12/2004 | Harel et al. | |
| 2005/0096514 A1 | 5/2005 | Starkebaum | |
| 2005/0149142 A1 | 7/2005 | Starkebaum | |
| 2005/0164925 A1 | 7/2005 | Jakubowski et al. | |
| 2005/0222638 A1 | 10/2005 | Foley et al. | |
| 2006/0064037 A1 | 3/2006 | Shalon et al. | |
| 2006/0074459 A1 | 4/2006 | Flesler et al. | |
| 2006/0085045 A1 | 4/2006 | Harel et al. | |
| 2006/0173238 A1 | 8/2006 | Starkebaum | |
| 2006/0184207 A1 | 8/2006 | Darvish et al. | |
| 2006/0264699 A1 | 11/2006 | Gertner | |
| 2007/0027493 A1 * | 2/2007 | Ben-Haim et al. | 607/40 |
| 2007/0051849 A1 | 3/2007 | Watts et al. | |
| 2007/0060812 A1 | 3/2007 | Harel et al. | |
| 2007/0060971 A1 | 3/2007 | Glasberg et al. | |
| 2007/0092446 A1 | 4/2007 | Haddad et al. | |
| 2007/0156177 A1 | 7/2007 | Harel et al. | |
| 2007/0179556 A1 | 8/2007 | Ben-Haim et al. | |
| 2007/0185540 A1 | 8/2007 | Ben-Haim et al. | |
| 2007/0299320 A1 | 12/2007 | Policker et al. | |
| 2008/0046062 A1 | 2/2008 | Camps et al. | |
| 2008/0058889 A1 | 3/2008 | Ben-Haim et al. | |
| 2008/0058891 A1 | 3/2008 | Ben-Haim et al. | |
| 2008/0065168 A1 | 3/2008 | Bitton et al. | |
| 2008/0178684 A1 | 7/2008 | Spehr | |
| 2009/0062893 A1 | 3/2009 | Spehr | |
| 2009/0088816 A1 | 4/2009 | Harel et al. | |
| 2009/0118797 A1 * | 5/2009 | Kliger et al. | 607/62 |
| 2009/0131993 A1 | 5/2009 | Rousso et al. | |
| 2009/0204063 A1 * | 8/2009 | Policker et al. | 604/26 |
| 2009/0281449 A1 | 11/2009 | Thrower et al. | |
| 2010/0228105 A1 * | 9/2010 | Policker et al. | 600/302 |
| 2010/0305468 A1 | 12/2010 | Policker et al. | |
| 2010/0324644 A1 | 12/2010 | Levi et al. | |

FOREIGN PATENT DOCUMENTS

| | | |
|---|---|---|
| WO | WO 97/41921 | 11/1997 |
| WO | WO 98/10830 | 3/1998 |
| WO | WO 99/03533 | 1/1999 |
| WO | WO 00/53257 | 9/2000 |
| WO | WO 01/10375 | 2/2001 |
| WO | WO 01/66183 | 9/2001 |
| WO | WO 01/91854 | 12/2001 |
| WO | WO 02/38217 | 5/2002 |
| WO | WO 02/053093 | 7/2002 |
| WO | WO 02/082968 | 10/2002 |
| WO | WO 03/045493 | 6/2003 |
| WO | WO 2004/021858 | 3/2004 |
| WO | WO 2004/112563 | 12/2004 |
| WO | WO 2004/112883 | 12/2004 |
| WO | WO 2005/007232 | 1/2005 |
| WO | WO 2005/023081 | 3/2005 |
| WO | WO 2005/087310 | 9/2005 |
| WO | WO 2006/018851 | 2/2006 |
| WO | WO 2006/045075 | 4/2006 |
| WO | WO 2006/073671 | 7/2006 |
| WO | WO 2006/087712 | 8/2006 |
| WO | WO 2006/087717 | 8/2006 |
| WO | WO 2006/097934 | 9/2006 |
| WO | WO 2006/102626 | 9/2006 |
| WO | WO 2006/129321 | 9/2006 |
| WO | WO 2006/107901 | 10/2006 |
| WO | WO 2006/119467 | 11/2006 |
| WO | WO 2006/129321 | 12/2006 |
| WO | WO 2007/080595 | 7/2007 |
| WO | WO 2008/117296 | 10/2008 |
| WO | WO 2008/139463 | 11/2008 |
| WO | WO 2011/092710 | 8/2011 |

OTHER PUBLICATIONS

An Office Action dated Nov. 16, 2010, which issued during the prosecution of U.S. Appl. No. 11/573,722.

An abstract entitled "Gastric myoelectrical pacing as therapy for morbid obesity: Preliminary results", by Cigaina, et al., Dec. 24, 2000.

An abstract entitled "Implantable gastric stimulator (IGS) as therapy for morbid obesity: Equipment, surgical technique and stimulation parameters", by Cigaina, et al., Dec. 24, 2000.

Stein et al., "Carrots and sticks: Impact of an incentive/disincentive employee flexible credit benefit plan on health status and medical costs", American Journal of Health Promotion, May/Jun. 1999, V5, I13, 5.

Giuffrida, "Should we pay the patient? Review of financial incentives to enhance patient compliance", Biomedical Journal, vol. 315, pp. 703-707, 1997.

An International Search Report and a Written Opinion, both date Oct. 28, 2008, which issued during the prosecution of Applicant's PCT/IL08/00646.

A Supplementary Partial European Search Report dated Feb. 20, 2009, which issued during the prosecution of Applicant's European Patent Application No. EP 02 72 7012.

An Examination Report dated Apr. 7, 2009, which issued during the prosecution of Applicant's European Patent Application No. EP 06 74 8690.

U.S. Appl. No. 60/259,925, filed Jan. 5, 2001.

U.S. Appl. No. 60/602,550, filed Aug. 18, 2004.

Paul Goode, et al., "Assessment of eating detection algorithm in gastric electrical stimulation device to treat subjects with T2DM", Presented on Oct. 25, 2007, 7th Annual Diabetes Technology Meeting, Oct. 25-27, 2007, San Francisco, CA, USA.

International Search Report and the Written Opinion Dated Sep. 2, 2011 From the International Searching Authority Re. Application No. PCT/IL 11/00116.

Office Action dated Jun. 12, 2012 in U.S. Appl. No. 11/573,722.

* cited by examiner

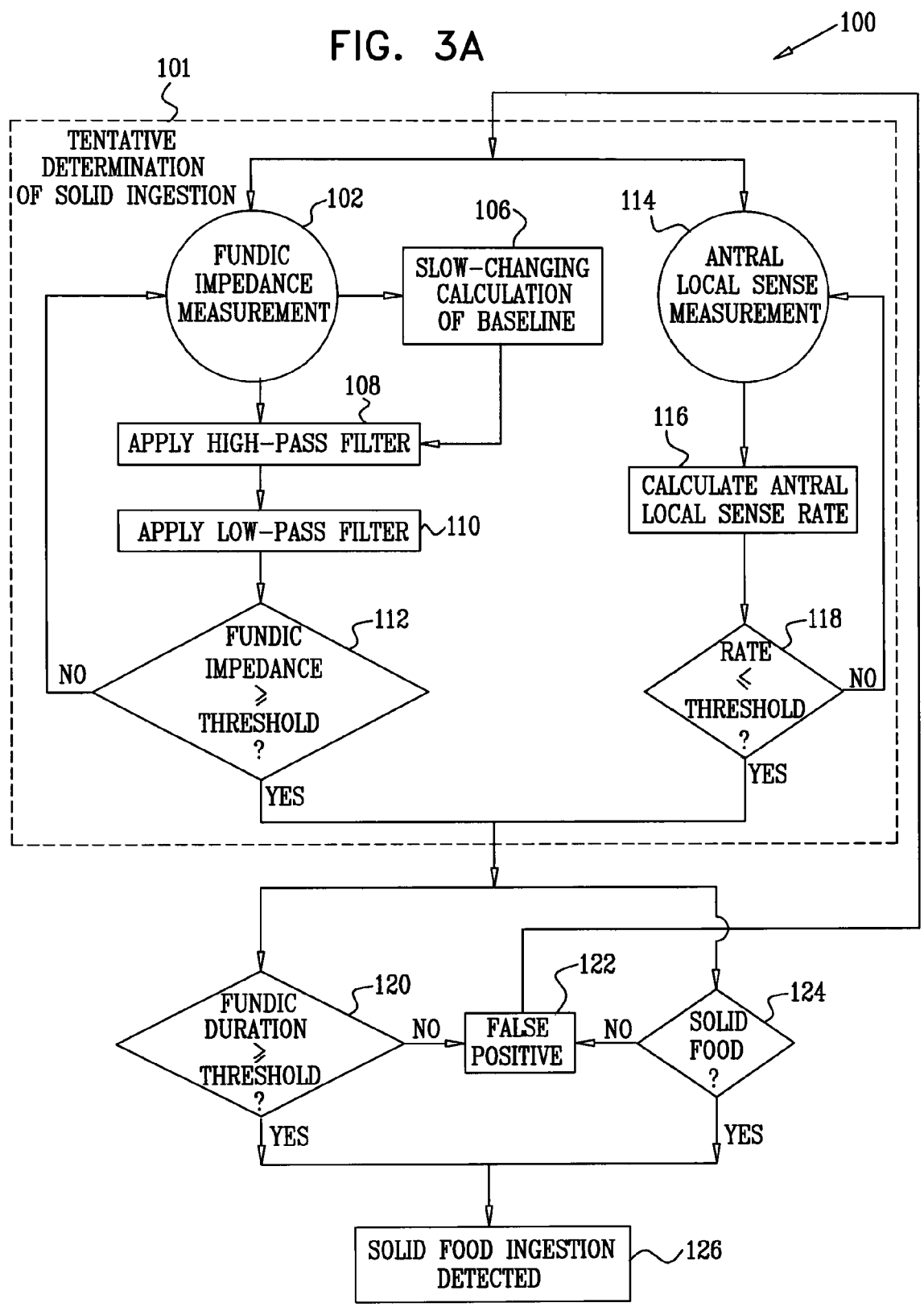

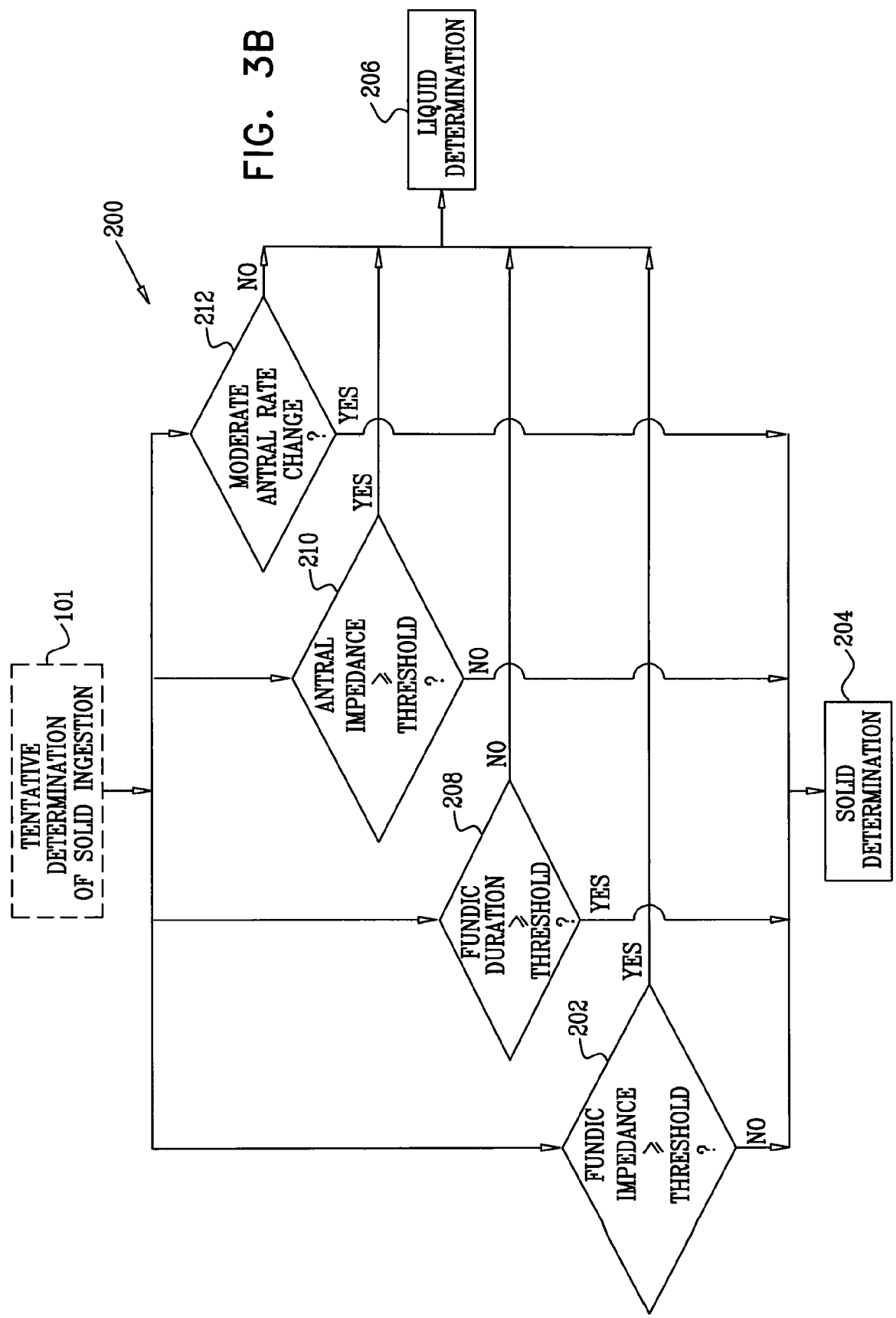

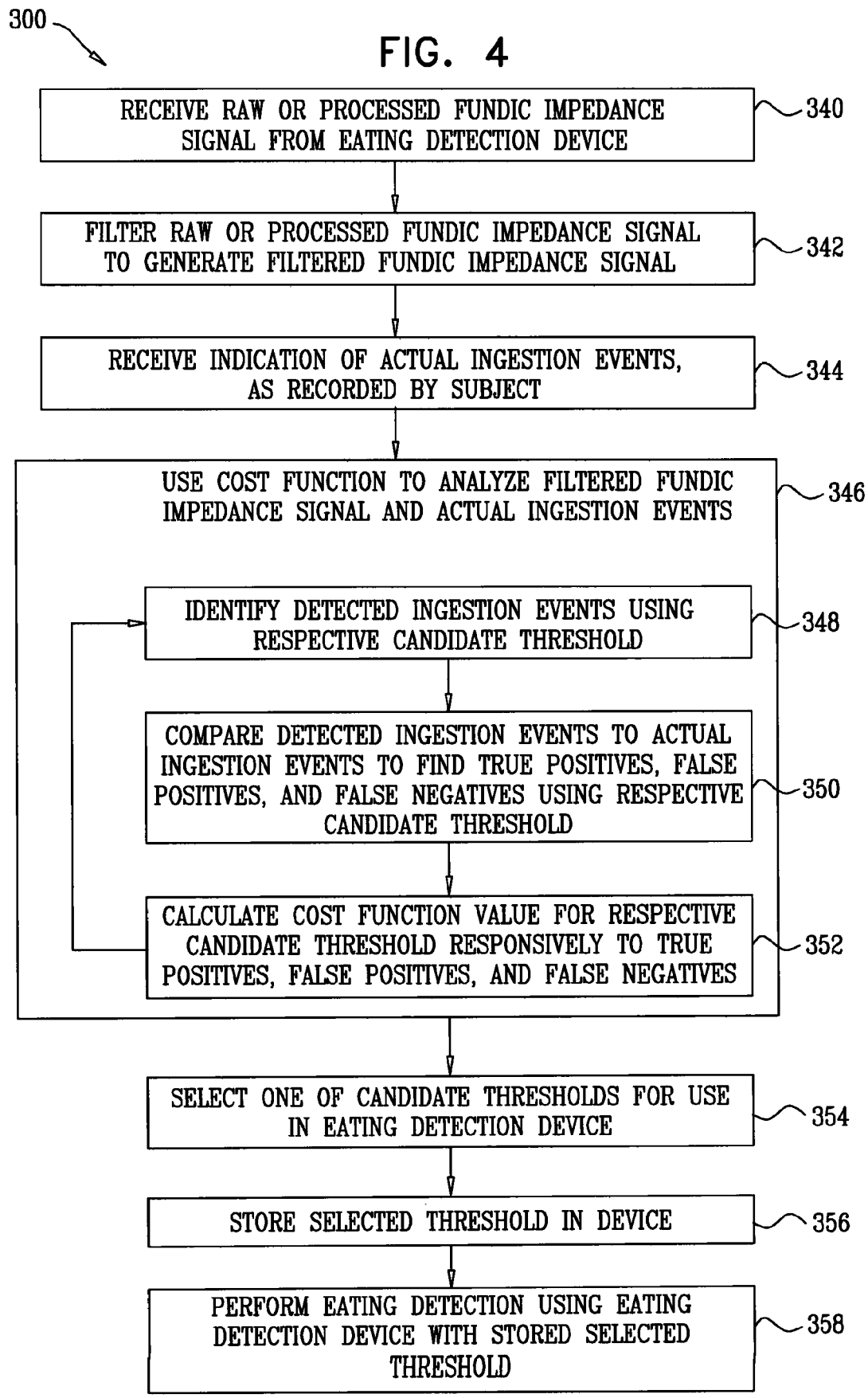

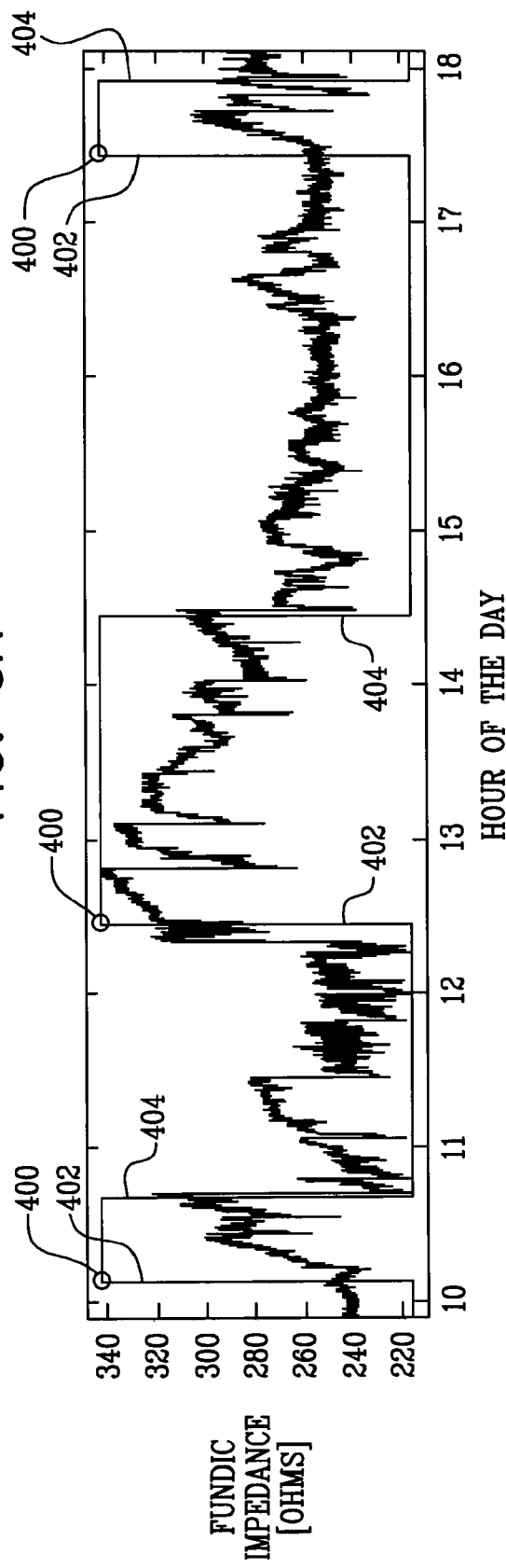
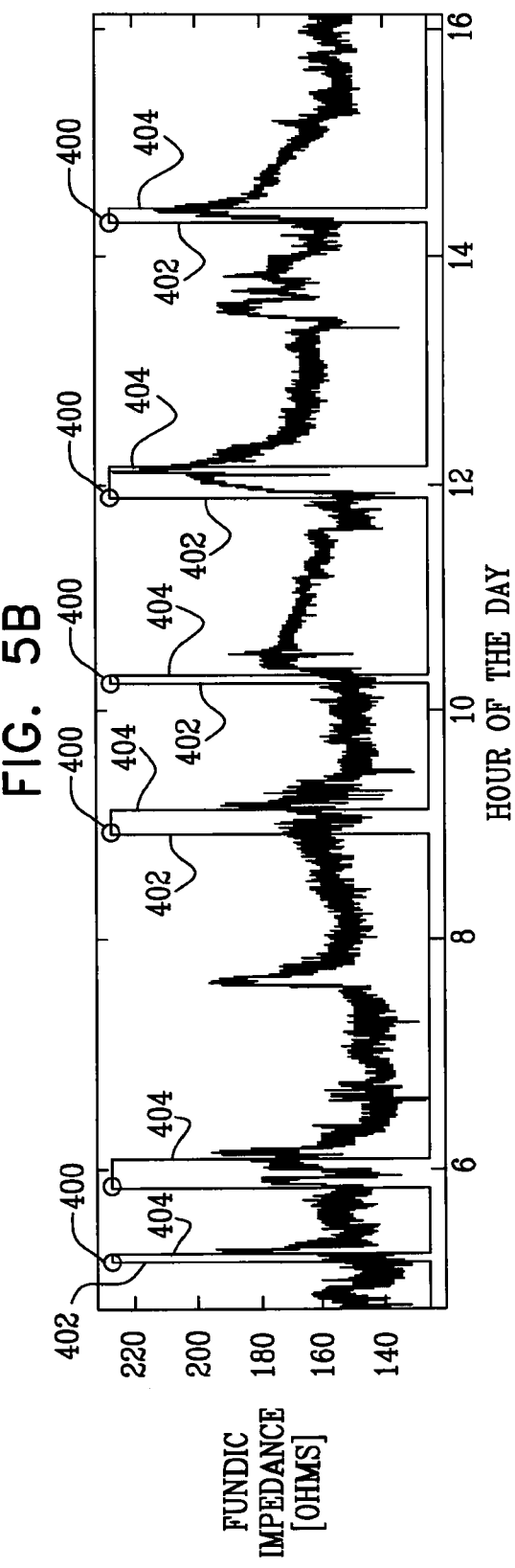
FIG. 5A
FIG. 5B

OPTIMIZATION OF THRESHOLDS FOR EATING DETECTION

CROSS-REFERENCE TO RELATED APPLICATIONS

The present application claims the benefit of U.S. Provisional Application 61/051,901, filed May 9, 2008, entitled, "Optimization of filters and parameters for eating detection," which is assigned to the assignee of the present application and is incorporated herein by reference.

FIELD OF THE INVENTION

The present invention relates generally to detecting ingestion of food, and specifically to techniques for optimizing ingestion detection parameters for use with invasive techniques and apparatus.

BACKGROUND OF THE INVENTION

Obesity is a difficult to treat chronic condition defined by a body mass index (BMI=mass/height$^2$ [kg/m$^2$]) greater than 30. For obese persons, excessive weight is commonly associated with increased risk of cardiovascular disease, diabetes, degenerative arthritis, endocrine and pulmonary abnormalities, gallbladder disease and hypertension. Additionally, such persons are highly likely to experience psychological difficulties because of lifestyle restrictions such as reduced mobility and physical capacity, due to back pain, joint problems, and shortness of breath. In severe cases, this can contribute to absenteeism and unemployment. Moreover, impairment of body image can lead to significant psychological disturbances. Repeated failures of dieting and exercise to resolve the problem of obesity can result in feelings of despair and the development of clinical depression.

Bariatric surgery is often recommended for persons suffering from morbid obesity. Preferably, the invasive treatment is accompanied by changes in lifestyle, such as improved regulation of eating habits and an appropriate exercise regimen. Such lifestyle changes are dependent upon the self-discipline and cooperation of the patient. Policker S et al., in an article entitled, "Electrical Stimulation of the Gut for the Treatment of Type 2 Diabetes: The Role of Automatic Eating Detection," J Diabetes Sci and Technol 2(5):906-912 (2008), relevant portions of which are incorporated herein by reference, review the performance of an automatic eating detection device that continuously senses changes in tissue impedance and initiates treatment sessions upon detection of eating.

PCT Patent Publication WO 02/082968 to Policker et al., relevant portions of which are incorporated herein by reference, describes apparatus and methods for detecting the occurrence of an eating event by a subject and analyzing the quantity and characteristics of the food ingested.

PCT Publication WO 06/018851 to Kliger et al., relevant portions of which are incorporated herein by reference, describes gastric apparatus including one or more sensors adapted to generate respective sensor signals responsive to activity of a gastrointestinal tract of a subject. A control unit is adapted to receive and analyze the sensor signals and to determine that an eating event has occurred, responsive to at least one of the sensor signals and a threshold. The control unit identifies an aspect of at least one of the sensor signals deriving from rhythmic activity of the gastrointestinal tract that is not indicative of current eating by the subject, and modifies the threshold responsive to the aspect of the signals that derives from activity that is not indicative of current eating.

U.S. Pat. No. 6,104,955 to Bourgeois, relevant portions of which are incorporated herein by reference, describes a method and apparatus for providing electrical stimulation of the gastrointestinal tract. The apparatus comprises an implantable pulse generator which may be coupled to the gastric system through one or more medical electrical leads. In the preferred embodiment the leads are coupled to the circular layer of the stomach. The pulse generator preferably comprises sensors for sensing gastric electrical activity, and in particular, whether peristaltic contractions are occurring. One embodiment detects gastric arrhythmias by periodically reverting into a sensed intrinsic gastric rhythm mode. In this mode the output of electrical stimulation is adjusted to only occur at an exceedingly slow rate. This slow rate of stimulation thus permits the gastrointestinal tissues to undergo an intrinsic depolarization so that the underlying intrinsic slow wave rate may be detected.

U.S. Pat. No. 5,995,872 to Bourgeois, relevant portions of which are incorporated herein by reference, describes a method and apparatus for providing electrical stimulation of the gastrointestinal tract. The apparatus comprises an implantable pulse generator which may be coupled to the gastric system through one or more medical electrical leads. In the preferred embodiment the leads are coupled to the circular layer of the stomach. The pulse generator preferably comprises sensors for sensing gastric electrical activity, and in particular, whether peristaltic contractions are occurring. In particular two sensors are included. The first sensor senses low frequency gastrointestinal electrical activity between the frequency of 0.017-0.25 Hz and the second sensor senses intrinsic gastrointestinal electrical activity between the frequency of 100-300 Hz, which occurs upon normal peristaltic contractions. The second sensor only senses for a preset period after low frequency gastrointestinal electrical activity has been sensed by the first sensor. The pulse generator further delivers stimulation pulse trains to the gastrointestinal tract at a period of time after low frequency gastrointestinal electrical activity has been sensed by the first sensor. If, however, the second sensor senses intrinsic gastrointestinal electrical activity between the frequency of 100-300 Hz, then the delivery of stimulation pulse trains to the gastrointestinal tract is inhibited. In such a manner the present invention detects the occurrence of normal peristaltic contractions and further provides electrical stimulation to the gastrointestinal tract if such normal peristaltic contractions are not detected.

The following patents and patent application publications, relevant portions of which are incorporated herein by reference, may be of interest:

U.S. Pat. No. 5,188,104 to Wernicke et al.
U.S. Pat. No. 6,571,127 to Ben-Haim et al.
US Patent Application Publication 2006/0173238 to Warren
US Patent Application Publication 2005/0222638 to Foley et al.

SUMMARY OF THE INVENTION

In some embodiments of the present invention, a method is provided for automatically setting a fundic impedance increase threshold value that is optimized for a given subject, for use in detecting ingestion by an eating detection device. The method begins by receiving a sensed fundic impedance signal sensed during an initial calibration period using implantable fundic local sense electrodes of the eating detection device. The sensed fundic impedance signal is filtered to generate a filtered fundic impedance signal. An indication is received of actual ingestion events during the initial calibration period, as recorded by the subject or a healthcare worker. A cost function is used to perform an analysis of the filtered fundic impedance signal and the actual ingestion events. Responsively to the analysis, a threshold is set, the crossing of which by the filtered fundic impedance signal is indicative of ingestion. The threshold is stored in a memory of the eating detection device, and is subsequently used by the device in an algorithm for detecting ingestion events.

In some embodiments of the present invention, the cost function is used to find each of plurality of cost function values for each of a plurality of respective candidate thresholds. To find each of the cost function values, an algorithm is performed that identifies detected ingestion events during the initial calibration period by comparing the filtered fundic impedance signal to the candidate threshold over the initial calibration period. The detected ingestion events are compared to the actual ingestion events recorded by the subject or the healthcare worker, in order to find how many of the detected ingestion events represent true positives, false positives, and false negatives. A cost function value is calculated for the respective candidate threshold responsively to the number of true positives, the number of false positives, and the number of false negatives. Once respective cost function values have been calculated for all of the candidate thresholds, one of the candidate thresholds is selected as the threshold to be used by the implantable eating detection device, responsively to the cost function values. Typically, the threshold is selected responsively to a ranking of the cost function values. For example, the candidate threshold may be selected that is associated with the lowest cost function value, or with the highest cost function value.

In some embodiments of the present invention, one or both of the following relationships among true positives (TP), false positives (FP), and false negatives (FN) are used in the cost function:

Sensitivity=TP/(TP+FN)

Positive Predictive Value (PPV)=TP/(TP+FP)

In some embodiments of the present invention, the following cost function is used to calculate the cost function values:

Cost Function=Sensitivity+PPVweighting*PPV wherein PPVweighting is a constant, typically having a value between 0 and about 10, such as between about 0.7 and about 1.3, e.g., about 1.0.

In some embodiments of the present invention, the eating detection device comprises a fundic sensor configured to be coupled to a fundic region of a stomach of the subject. An implantable control unit or external controls detect the ingestion of predominantly solid food upon finding that an increase in fundic impedance measured by the fundic sensor vs. a baseline level (measured during a pre-intake period) is greater than a threshold value. The threshold value is typically individually set for each subject using the method described above.

In some embodiments of the present invention, the eating detection device further comprises one or more current-application electrodes, which are configured to be coupled to a stomach of the subject, and to apply an electrical signal to the stomach responsively to detection of ingestion of the subject by the eating detection device.

In some embodiments of the present invention, the eating detection device further comprises a gastric band, configured to mechanically modify a volume of a stomach of the subject. The gastric band is configured to be placed around the stomach and to be tightened so as to cause a narrowing of the stomach, thereby reducing the volume of the stomach. For some applications, the gastric band is configured to be tightened and loosened in real time, responsively to signals received from the control unit. Tightening of the band causes a narrowing of the stomach, thereby reducing the volume of the stomach. For some applications, the gastric band is tightened responsively to the indication of ingestion of solid food but not responsively to the indication of ingestion of a liquid. Alternatively or additionally, reducing the volume of the stomach responsively to the indication of ingestion of solid food but not responsively to the indication of ingestion of a liquid includes applying an electrical signal to the stomach, and configuring the electrical signal to modify a contraction pattern of one or more muscles of the stomach.

In some embodiments of the present invention, the collected data are stored and intermittently uploaded to an external computer, typically by a wireless communications link, for review by the subject's physician, to enable monitoring of the subject's adherence to a dietary regimen, and/or for calibrating the fundic impedance increase threshold value described above.

"Food," as used in the present application including the claims, is to be understood as including both solid and liquid food, unless otherwise indicated.

There is therefore provided, in accordance with an embodiment of the present invention, a method including:

providing a fundic impedance signal of a subject sensed during an initial calibration period using at least one implantable fundic sensor of an eating detection device;

receiving an indication of actual ingestion events of the subject during the initial calibration period;

using a cost function, performing an analysis of the fundic impedance signal and the actual ingestion events;

responsively to the analysis, setting a threshold, the crossing of which by the fundic impedance signal is indicative of ingestion; and storing the threshold in a memory of the eating detection device.

For some applications, providing the fundic impedance signal includes receiving a sensed fundic impedance signal of the subject sensed during the initial calibration period using the at least one implantable fundic sensor, and filtering the sensed fundic impedance signal to generate a filtered fundic impedance signal, and performing the analysis includes performing the analysis of the filtered fundic impedance signal and the actual ingestion events.

For some applications, receiving the sensed fundic impedance signal includes receiving a representative sample of a raw fundic impedance signal, and filtering includes filtering the representative sample of the raw fundic impedance signal to generate the filtered fundic impedance signal.

For some applications, providing the fundic impedance signal includes receiving a filtered fundic impedance signal from the eating detection device, and performing the analysis includes performing the analysis of the filtered fundic impedance signal and the actual ingestion events.

In an embodiment, performing the analysis and setting the threshold include performing the analysis and setting the threshold by the eating detection device.

In an embodiment, performing the analysis and setting the threshold include performing the analysis and setting the threshold by a computer workstation separate from the eating detection device, and storing the threshold in the memory of the eating detection device includes transmitting, by the workstation, the threshold to the eating detection device.

In an embodiment, the threshold is one of a plurality of candidate thresholds, performing the analysis includes using the cost function to find each of a plurality of cost function values for each of the respective candidate thresholds by identifying detected ingestion events during the initial calibration period by comparing the fundic impedance signal to the candidate threshold over the initial calibration period; comparing the detected ingestion events to the actual ingestion events to find a number of the detected ingestion events that represent true positives, a number of the detected ingestion events that represent false positives, and a number of the actual ingestion events that represent false negatives; and calculating the cost function value responsively to the number of the true positives, the number of the false positives, and the number of the false negatives, and setting the threshold includes selecting one of the candidate thresholds as the threshold responsively to the cost function values.

For some applications, selecting the one of the candidate thresholds includes selecting the one of the candidate thresholds responsively to a ranking of the cost function values. For example, selecting the one of the candidate thresholds may include selecting the one of the candidate thresholds associated with a lowest or nearly lowest one of the cost function values. Alternatively, selecting the one of the candidate thresholds may include selecting the one of the candidate thresholds associated with a highest or nearly highest one of the cost function values.

In an embodiment, calculating the cost function value includes calculating the cost function value responsively to a measure of sensitivity of the algorithm and a measure of positive predictive value of the algorithm. For some applications, calculating the cost function value includes calculating the measure of sensitivity responsively to the number of the true positives and the number of the false negatives. For example, calculating the measure of sensitivity may include calculating the quotient of the number of the true positives divided by a sum of the number of the true positives and the number of the false negatives.

For some applications, calculating the cost function value includes calculating the measure of positive predictive value responsively to the number of the true positives and the number of the false positives. For example, calculating the measure of positive predictive value may include calculating the quotient of the number of the true positives divided by a sum of the number of the true positives and the number of the false positives.

For some applications, calculating the cost function includes calculating a sum of the measure of sensitivity and a product of the measure of positive predictive value and a weighting factor. For example the weighting factor may be between 0.7 and 1.3, such as 1.0.

For some applications, calculating the cost function includes calculating a product of the measure of sensitivity and the measure of positive predictive value and a weighting factor.

For some applications, calculating the cost function includes performing one or more mathematical operations on the number of true positives, the number of false positives, and the number false negatives, using one or more coefficients as respective weighting factors.

In an embodiment, the method further includes, during a treatment period after the initial calibration period:
sensing, using the at least one fundic sensor of the eating detection device, a treatment sensed fundic impedance signal;
filtering, by the eating detection device, the treatment sensed fundic impedance signal to generate a treatment filtered fundic impedance signal; and identifying, by the eating detection device, a treatment period ingestion event by comparing the treatment filtered fundic impedance signal to the selected one of the thresholds stored in the memory of the eating detection device.

For some applications, the method further includes, responsively to identifying the treatment period ingestion event, applying a treatment to the subject by the eating detection device.

For some applications, the actual ingestion events are actual solid food ingestion events, and receiving the indication of the actual ingestion events includes receiving the indication of the actual solid food ingestion events by the subject during the initial calibration period.

For some applications, providing the fundic impedance signal includes providing a set of filtered fundic impedance increase vs. baseline values, and setting the threshold includes setting a fundic impedance increase vs. baseline threshold.

There is further provided, in accordance with an embodiment of the present invention, apparatus for use with an eating detection device having a memory and at least one implantable fundic sensor, the apparatus including:
an interface, configured to communicate with the eating detecting device; and
a processor, configured to receive, via the interface, a fundic impedance signal of a subject sensed during an initial calibration period using the at least one implantable fundic sensor of the eating detection device; to receive an indication of actual ingestion events of the subject during the initial calibration period; using a cost function, to perform an analysis of the fundic impedance signal and the actual ingestion events; responsively to the analysis, to set a threshold, the crossing of which by the fundic impedance signal is indicative of ingestion; and to store, via the interface, the threshold in the memory of the eating detection device.

For some applications, the processor is configured to filter the fundic impedance signal to generate a filtered fundic impedance signal, and to perform the analysis of the filtered fundic impedance signal and the actual ingestion events.

For some applications, the fundic impedance signal includes a filtered fundic impedance signal, and the processor is configured to receive the filtered fundic impedance signal from the eating detection device, via the interface, and to perform the analysis of the filtered fundic impedance signal and the actual ingestion events.

In an embodiment, the threshold is one of a plurality of candidate thresholds, the processor is configured to perform the analysis by using the cost function to find each of a plurality of cost function values for each of the respective candidate thresholds by identifying detected ingestion events during the initial calibration period by comparing the fundic impedance signal to the candidate threshold over the initial calibration period; comparing the detected ingestion events to the actual ingestion events to find a number of the detected ingestion events that represent true positives, a number of the detected ingestion events that represent false positives, and a number of the actual ingestion events that represent false negatives; and calculating the cost function value responsively to the number of the true positives, the number of the false positives, and the number of the false negatives, and the processor is configured to set the threshold by selecting one of the candidate thresholds as the threshold responsively to the cost function values.

There is still further provided, in accordance with an embodiment of the present invention, apparatus including:

one or more implantable fundic sensors, configured to be applied to a fundus of a subject, and to generate a fundic impedance signal; and a control element, which includes a memory, and which is configured to:

receive the fundic impedance signal sensed during an initial calibration period, receive an indication of actual ingestion events of the subject during the initial calibration period, using a cost function, perform an analysis of the fundic impedance signal and the actual ingestion events, responsively to the analysis, set a threshold, the crossing of which by the fundic impedance signal is indicative of ingestion, and store the threshold in the memory.

For some applications, the control element is configured to filter the fundic impedance signal to generate a filtered fundic impedance signal, and perform the analysis of the filtered fundic impedance signal and the actual ingestion events.

In an embodiment, the threshold is one of a plurality of candidate thresholds, the control element is configured to perform the analysis by using the cost function to find each of a plurality of cost function values for each of the respective candidate thresholds by identifying detected ingestion events during the initial calibration period by comparing the fundic impedance signal to the candidate threshold over the initial calibration period; comparing the detected ingestion events to the actual ingestion events to find a number of the detected ingestion events that represent true positives, a number of the detected ingestion events that represent false positives, and a number of the actual ingestion events that represent false negatives; and calculating the cost function value responsively to the number of the true positives, the number of the false positives, and the number of the false negatives, and the control element is configured to set the threshold by selecting one of the candidate thresholds as the threshold responsively to the cost function values.

In an embodiment, the control element is configured to, during a treatment period after the initial calibration period, receive, from the at least one fundic sensor, a treatment sensed fundic impedance signal, filter the treatment sensed fundic impedance signal to generate a treatment filtered fundic impedance signal, and identify a treatment period ingestion event by comparing the treatment filtered fundic impedance signal to the selected one of the thresholds stored in the memory of the eating detection device. For some applications, the apparatus further includes an implantable treatment unit, and the control element is configured to drive the implantable treatment unit to apply a treatment to the subject, responsively to identifying the treatment period ingestion event.

There is additionally provided, in accordance with an embodiment of the present invention, a computer software product for use with an eating detection device having a memory and at least one implantable fundic sensor, the product including a tangible computer-readable medium in which program instructions are stored, which instructions, when read by a computer, cause the computer to receive a fundic impedance signal of a subject sensed during an initial calibration period using the at least one implantable fundic sensor of the eating detection device; to receive an indication of actual ingestion events of the subject during the initial calibration period; using a cost function, to perform an analysis of the fundic impedance signal and the actual ingestion events; responsively to the analysis, to set a threshold, the crossing of which by the fundic impedance signal is indicative of ingestion; and to store the threshold in the memory of the eating detection device.

In an embodiment, the threshold is one of a plurality of candidate thresholds, the instructions, when read by the computer, cause the computer to perform the analysis by using the cost function to find each of a plurality of cost function values for each of the respective candidate thresholds by identifying detected ingestion events during the initial calibration period by comparing the fundic impedance signal to the candidate threshold over the initial calibration period; comparing the detected ingestion events to the actual ingestion events to find a number of the detected ingestion events that represent true positives, a number of the detected ingestion events that represent false positives, and a number of the actual ingestion events that represent false negatives; and calculating the cost function value responsively to the number of the true positives, the number of the false positives, and the number of the false negatives, and the instructions, when read by the computer, cause the computer to set the threshold by selecting one of the candidate thresholds as the threshold responsively to the cost function values.

The present invention will be more fully understood from the following detailed description of embodiments thereof, taken together with the drawings, in which:

BRIEF DESCRIPTION OF THE DRAWINGS

FIG. 3A is a flow chart illustrating an algorithm for detecting ingestion of solid food, in accordance with an embodiment of the present invention;

FIG. 3B is a flow chart illustrating an algorithm for differentiating between ingestion of solid and liquid food, in accordance with an embodiment of the present invention;

FIG. 4 is a flow chart illustrating an algorithm for setting a fundic increase threshold value, in accordance with an embodiment of the present invention;

FIGS. 5A and 5B are graphs showing raw measured fundic impedance signals for two human subjects measured in an experiment conducted in accordance with an embodiment of the present invention.

DETAILED DESCRIPTION OF EMBODIMENTS

Figure 1A:
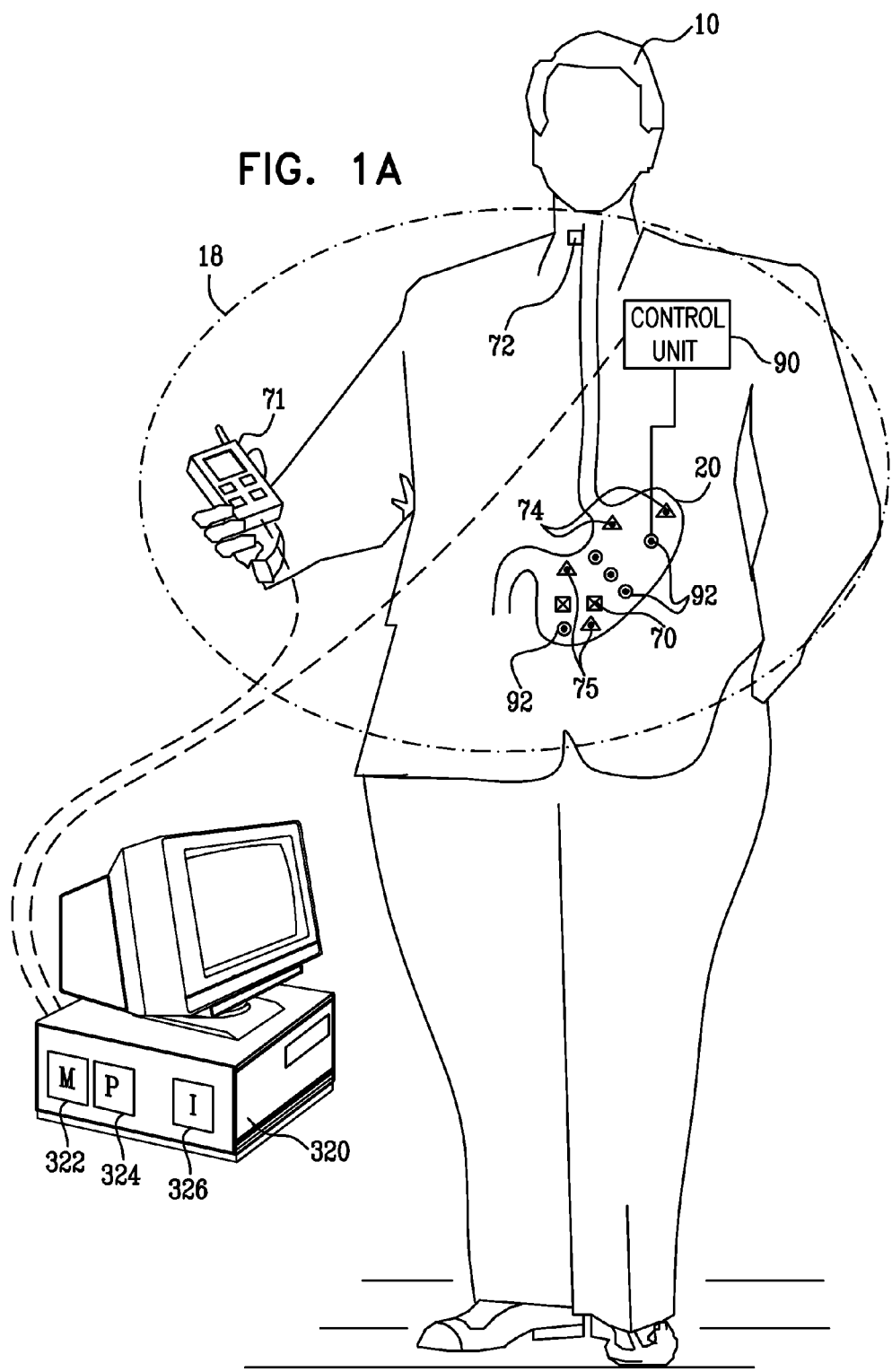
FIG. 1A is a schematic illustration of apparatus for detecting the ingestion and/or content of liquid and/or solid food, in accordance with an embodiment of the present invention.

FIG. 1A is a schematic illustration of apparatus 18 for detecting the ingestion and/or content of liquid and/or solid food, in accordance with an embodiment of the present invention. Apparatus 18 comprises fundic local sense electrodes 74, a control unit 90, operator controls 71, and, optionally, antral local sense electrodes 75. For some applications, operator controls 71 are implemented in dedicated hardware, while for other applications, a commercially available device, such as a cellular telephone, PDA, or other handheld device, is programmed in software to carry out the functions of the operator controls. For some applications, apparatus 18 further comprises an implantable treatment unit, which may comprise one or more current-application electrodes 92; mechanical sensors 70; and/or supplemental sensors 72. In an embodiment, fundic local sense electrodes 74 are replaced or supplemented by other fundic change sensors, such as strain gauges, which similarly indicate distension of the fundus. Alternatively or additionally, antral local sense electrodes 75 are replaced or supplemented by other antral change sensors, such as strain gauges, which similarly indicate distension of the antrum. As used in the claims, a "control element" comprises operator controls 71 and/or control unit 90, such that the control element may be implantable or external to the subject, or a portion of the control element may be implantable and another portion external.

Electrodes 74, 75, and 92 are typically coupled to the serosal layer of a stomach 20 of a subject 10 and/or inserted into the muscular layer of the stomach in the fundic and antral regions. For some applications, fundic local sense electrodes 74 are placed about 2.5 cm apart, approximately 2 cm inferior to the gastroesophageal junction, and, if provided, antral local sense electrodes 75 are placed about 3 cm apart, approximately 3 cm above the pylorus. Alternatively or additionally, the electrodes are coupled elsewhere on the stomach, gastrointestinal tract, or to other suitable locations in or on the subject's body. The number of electrodes and sensors, as well as the positions thereof, are shown in FIG. 1A by way of example, and other sites on stomach 20 or in or on the subject's body are appropriate for electrode and sensor placement in other applications of the present invention. Different types of electrodes known in the art are typically selected based on the specific condition of the subject's disorder, and may comprise stitch, coil, screw, patch, basket, needle and/or wire electrodes, or substantially any other electrode known in the art of electrical stimulation or sensing in tissue.

Figure 1B:
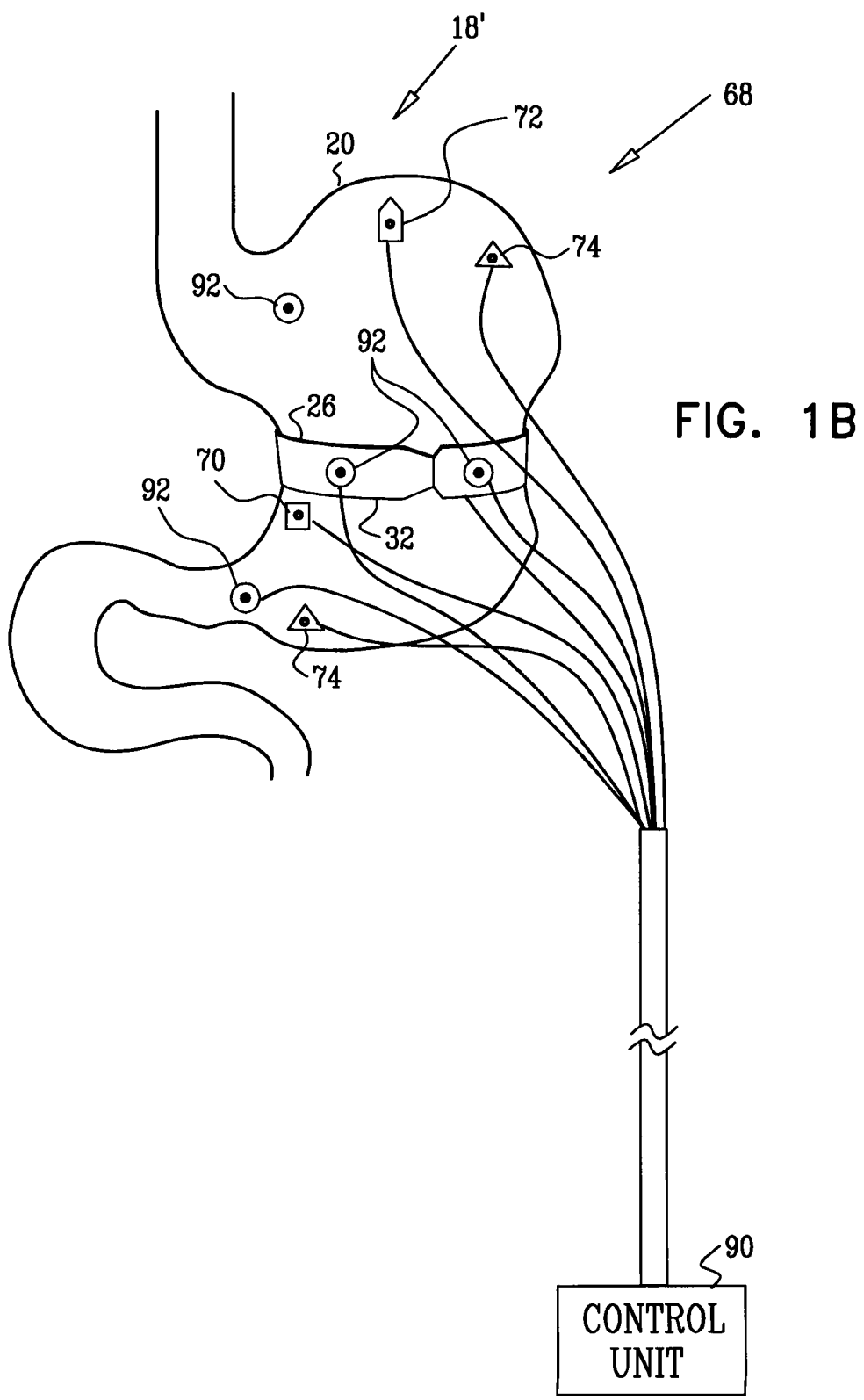
FIG. 1B is a schematic illustration of gastric control apparatus comprising an adjustable gastric band, in accordance with an embodiment of the present invention.

Reference is now made to FIG. 1B, which schematically illustrates gastric control apparatus 18', in accordance with an embodiment of the present invention. For the sake of simplicity, like elements to those described with respect to apparatus 18 shown in FIG. 1A are given the same reference numerals, and the following description details mainly the differences between apparatus 18 and apparatus 18'. Apparatus 18' comprises implantable or external control unit 90, and the implantable treatment unit, which comprises, as an alternative for or an addition to current application electrodes 92, a gastric band 32, configured to mechanically and/or electrically modify a volume of stomach 20. Gastric band 32 is configured to be placed around stomach 20 and to be tightened so as to cause a narrowing of stomach 20, thereby reducing the volume of the stomach. Like apparatus 18, apparatus 18' typically further comprises one or more sensors 70, 74, 75, and/or 72, as described hereinabove with reference to FIG. 1A. In an embodiment, one or more of the sensors (e.g., mechanical sensor 70) are fixed to an inner surface of gastric band 32.

Control unit 90 of apparatus 18' is configured to receive one or more signals from sensors 70, 74, 75, and/or 72, to analyze the signals, and, responsively to the analysis, to drive gastric band 32 to adjust in real-time the magnitude of stomach volume reduction. The reduced stomach volume increases the sensation of satiety felt by the subject compared to that which would be felt without such stomach volume reduction, and therefore generally reduces the subject's appetite so as to treat obesity of the subject. Such reduction is believed by the inventors to increase a sensation of satiety felt by the subject compared to that which was felt prior to tightening of the band. For some applications, control unit 90 drives current to one or more of application electrodes 92 to apply an electrical signal to the stomach responsively to the analysis. This signal may be delivered in addition to or instead of the driving of gastric band 32. Typically, the gastric band is configured such that the cross-sectional area of the stomach is reduced by at least 20%, and the control unit is configured to maintain this reduction in at least one region of the stomach for a period of at least one minute. It is to be understood that for some applications, greater or lesser reductions in cross-sectional area may be desirable, and these may be maintained for periods greater or less than one minute.

For some applications, active control of the size of gastric band 32 (particularly in combination with selective activation thereof in response to a determination of solid matter ingestion) reduces the frequency of follow-up visits to a doctor and/or the number of times that the level of band constriction is adjusted.

For some applications, apparatus 18 or 18' is implanted in subject 10 in a manner generally similar to that used to implant gastric pacemakers or other apparatus for stimulating or sensing in the gastrointestinal tract that are known in the art. As appropriate, techniques described in one or more of the references cited in the Background section of the present patent application may be adapted for use with these embodiments of the present invention. For some applications, electrode assemblies and/or techniques for implanting the electrodes are used which are described in PCT Publication WO 07/080,595 to Levi et al., relevant portions of which are incorporated herein by reference. Other methods and apparatus which may be useful in carrying out some embodiments of the present invention are described in U.S. Provisional Patent Application 60/259,925, and in the above-cited PCT publication, and in U.S. Pat. No. 6,600,953, relevant portions of all of which are incorporated herein by reference.

Reference is again made to FIG. 1B. As mentioned above, apparatus 18' may comprise one or more current application electrodes 92. Typically, control unit 90 drives current application electrodes 92 to apply an electrical signal to tissue of stomach 20, or another site of the GI.

For some applications, at least one of fundic local sense electrodes 74 is placed just proximal to gastric band 32 (i.e., on the wall that defines the pouch created by the band). In the case of a bipolar fundic lead, the other electrode 74 is typically implanted under the band (i.e., covered by the band, and optionally fixed to the band) or just distal to the band. In the case of a unipolar fundic lead, the single electrode 74 is typically placed proximal to the band. Alternatively, fundic local sense electrodes 74 are coupled to other sites of the fundus.

The circumference of gastric band 32 is bidirectionally adjustable in real time responsive to input from control unit 90. The gastric band typically, but not necessarily, utilizes one or more of the following techniques for controllably adjusting the circumference thereof:

Gastric band 32 comprises a motor, such as a linear motor or a rotary motor, which is configured to contract and expand gastric band 32. For example, motorized adjustment techniques may be used that are described in U.S. Pat. No. 6,067,991, U.S. Pat. No. 6,454,699, US Patent Application Publication 2003/0066536, and/or US Patent Application Publication 2001/0011543, relevant portions of all of which are incorporated herein by reference.

At least a portion of gastric band 32 comprises a temperature-sensitive material, the compliance and/or length of which varies in response to temperature changes. Control unit 90 applies changes in temperature to the material so as to achieve a desired stomach volume.

Gastric band 32 comprises a portion that is inflatable through a fill port. For example, an inner surface of the band may comprise the inflatable portion. Typically, the portion is inflated with a liquid, such as saline solution. The inflatable portion is typically connected by a tube to a balancing reservoir that is implanted under the skin of the subject. Band 32 further comprises a pump, which, responsive to input from control unit 90, transfers determined volumes of liquid in a closed circuit from the band to the reservoir or vice versa, to adjust the circumference of the band.

Adjustable band inflation techniques are used that are described in U.S. Pat. Nos. 5,938,669, 6,460,543, 6,453,907, and/or 6,454,699, and/or in US Patent Application Publication 2001/0011543, relevant portions of all of which are incorporated herein by reference.

Other techniques described in one or more of the publications referred to in the Background of the Invention are utilized for controllably adjusting the circumference of gastric band 32.

Figure 2:
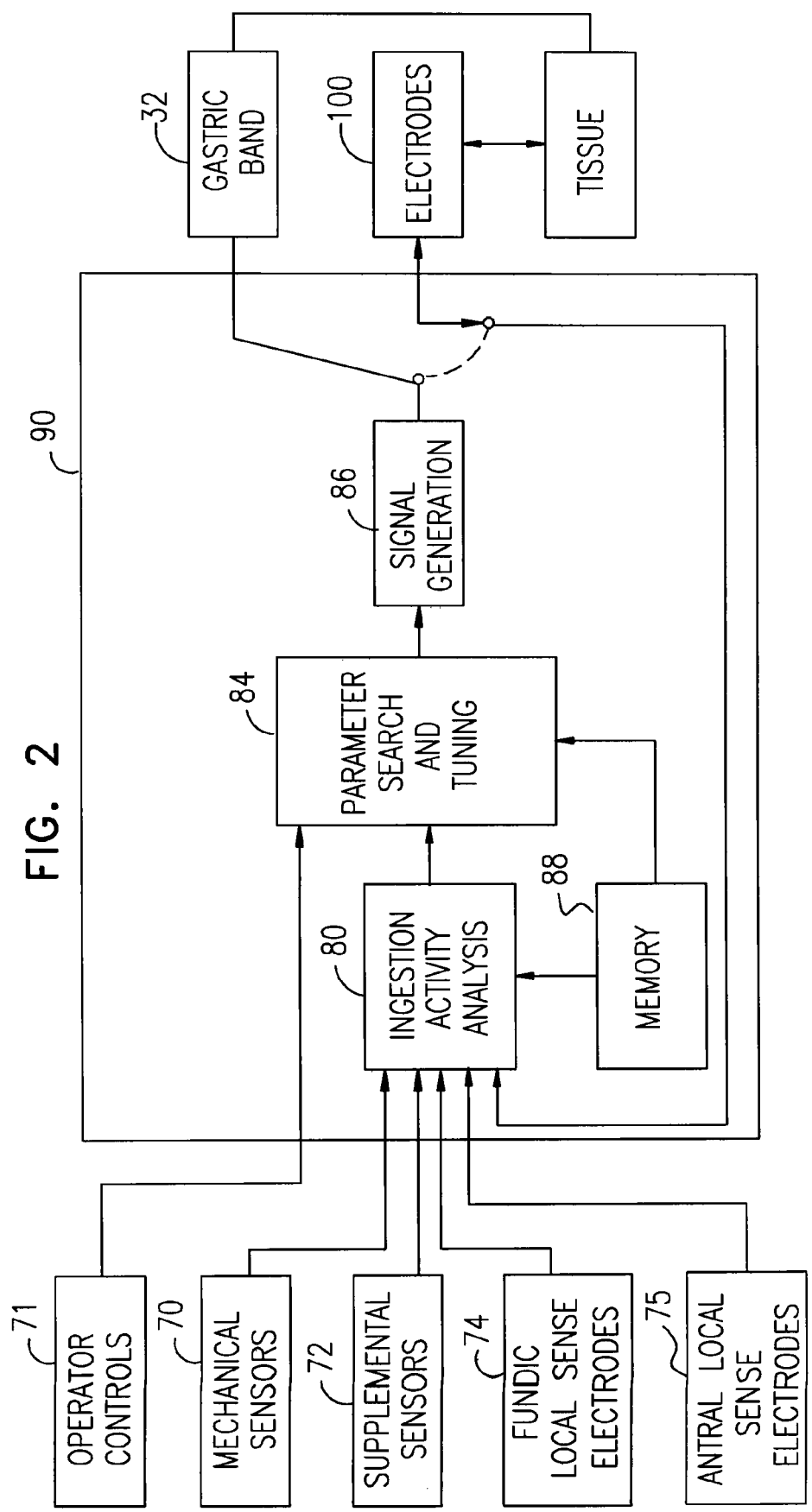
FIG. 2 is a schematic block diagram illustrating details of operation of a control unit of the apparatus of FIG. 1A or FIG. 1B, in accordance with an embodiment of the present invention.

FIG. 2 is a schematic block diagram illustrating details of operation of control unit 90 of apparatus 18 and 18', in accordance with an embodiment of the present invention. Control unit 90 is implanted in subject 10, and receives signals from fundic local sense electrodes 74, and, if provided, antral local sense electrodes 75, mechanical sensors 70, and/or supplemental sensors 72. These sensors and electrodes are typically configured to provide an "ingestion activity analysis" block 80 of the control unit with information about food ingestion and/or the present state of the stomach.

Analysis block 80 performs the ingestion analyses described hereinbelow. In order to improve the accuracy of the analyses described hereinbelow, analysis block 80 is typically calibrated by measuring the appropriate response criteria of stomach 20 of subject 10 to various types of solid and liquid food, such as described hereinbelow.

For some applications, analysis block 80 stores the results of its analysis in a memory block 88 of control unit 90, and these results are later uploaded to an external computer workstation, typically by a wireless communications link, for review by the subject's physician. Alternatively or additionally, analysis block 80 conveys results of its analysis of the inputs from mechanical sensors 70, supplemental sensors 72, and local sense electrodes 74, to a "parameter search and tuning" block 84 of control unit 90. The parameter search and tuning block adapts (a) the threshold values indicative of ingestion, by checking that an indicated ingestion event corresponds to an actual ingestion event, and (b) the threshold values indicative of food content (solid vs. liquid), by checking that an indicated food content correspondents to an actual ingested food content. For example, the parameter search and tuning block may rely on the subject to periodically verify or deny an ingestion event by using operator controls 71, or to periodically enter an indication of food content (solid vs. liquid) by using operator controls 71. In an embodiment, a false positive indication of an ingestion event causes one or more of the threshold values to be modified (e.g., increased), while a false negative may cause one or more of the threshold values to be decreased. Alternatively or additionally, an incorrect determination of food content causes one or more of the threshold values to be modified. For some applications, the parameter search and tuning block performs the threshold setting techniques described hereinbelow with reference to FIG. 4.

In an embodiment, apparatus 18 or 18' is calibrated using calibration techniques described in the above-mentioned PCT Publication WO 06/018851, mutatis mutandis. In an embodiment, algorithms and/or pseudo-code described in the '851 publication, mutatis mutandis, are used to determine the impedance and/or other thresholds described hereinabove.

In an embodiment of the present invention, control unit 90 further comprises a signal generation block 86, which drives current-application electrodes 92 to apply an electrical signal to tissue of stomach 20, or another site of the GI tract. For example, the electrical signal may include an ingestion-control signal, a satiety inducing signal, or a discomfort-inducing signal. For example, techniques may be used that are described in one or more of the following patent applications, relevant portions of all of which are incorporated herein by reference:

U.S. Provisional Patent Application 60/259,925, filed Jan. 5, 2001, entitled, "Regulation of eating habits";

PCT Publication WO 02/053093;

PCT Publication WO 05/007232;

U.S. Pat. No. 6,600,953; and/or

PCT Publication WO 06/018851.

Alternatively or additionally, signal control unit 90 activates gastric band 32 to tighten or loosen. For example, gastric band 32 may have two or more levels of tightening, and control unit 90 may cause tightening or loosening of the gastric band, thus selecting between these tightening levels. For example, the gastric band may have two tightening levels: a relatively tight level and a relatively loose, resting level. Upon detection that an ingested food is predominantly liquid or has a significant liquid component, control unit 90 may cause tightening of the gastric band to the tighter level. After a predetermined period of time or after a determination that liquid is no longer being ingested, control unit 90 may cause loosening of the gastric band to its resting level. Alternatively or additionally, the band may have a third, even looser tightening level. For example, upon detection that ingesta are predominantly a non-caloric liquid (such as water), control unit 90 may cause loosening of the gastric band to the loosest level, to allow unrestricted water consumption.

While FIG. 2 depicts a single control unit, this is solely by way of example. In some embodiments, two or more control units may be used, one of which controls at least gastric band 32, and another of which controls at least one of current application electrodes 92.

For some applications, one or more of the adjustable band inflation techniques are used that are described in U.S. Pat. Nos. 5,938,669, 6,460,543, 6,453,907, and/or 6,454,699, and/or in US Patent Application Publication 2001/0011543, relevant portions of all of which are incorporated herein by reference. Alternatively or additionally, other techniques known in the art (e.g., techniques described in one or more of the publications referred to in the Background of the Invention) are utilized for controllably adjusting the circumference of gastric band 32.

Reference is again made to FIG. 1A. In an embodiment of the present invention, operator controls 71 comprise a handheld portable device, which comprises a device wireless communication module, and is configured to provide a food diary for a subject, for aiding in behavior modification related to food intake, such as weight loss. Apparatus 18 or 18' comprises an implantable wireless device communication module, which is coupled to control unit 90. The control unit is configured to drive the implantable wireless device communication module to wirelessly transmit, to the device wireless communication module, an indication of the extent to which the ingested food includes the solid food matter, as determined using one or more techniques described herein. The handheld portable device is configured to record the indication in the food diary. For some applications, in addition to transmitting the indication, control unit 90 adjusts the circumference of gastric band 32 (shown in FIG. 1B) responsively to the indication, as described hereinabove.

Reference is made to FIG. 3A, which is a flow chart illustrating an impedance algorithm 100 for detecting ingestion of solid food, in accordance with an embodiment of the present invention. Algorithm 100 is adapted to minimize false positive detections of ingestion of solid food. For some applications, algorithm 100 detects ingestion of solid or liquid food. For some applications, algorithm 100 begins by making a tentative determination of ingestion of solid food, at a tentative solid ingestion step 101. Typically, the algorithm makes this determination based on an analysis of fundic impedance, as described hereinbelow with reference to steps 102 through 112, and, optionally, additionally based on an analysis of antral local sense rate, as described hereinbelow with references to steps 114 to 118. For some applications, the algorithm makes the tentative determination if either one of these analyses indicates the occurrence of ingestion, while for other applications, the algorithm makes the tentative determination only if both of these analyses indicate the occurrence of ingestion. The control unit typically performs these analyses generally in parallel, using software and/or hardware techniques for parallel execution of the algorithm, as known in the art. For some applications, the control unit instead makes a final, rather than tentative, determination at steps 102 through 112, or steps 102 through 118, and steps 120 through 124 of algorithm 100 are omitted. For some applications, all or a portion of algorithm 100 is performed using techniques described in above-mentioned U.S. Provisional Application 61/051,901, filed May 9, 2008, entitled, "Optimization of filters and parameters for eating detection."

For making the tentative determination of ingestion based on fundic impedance, algorithm 100 has as input a fundic impedance measurement 102, generated by fundic local sense electrodes 74, which are placed on or in the fundus of stomach 20 (FIGS. 1A and 1B). Fundic local sense electrodes 74 comprise two or more electrodes through which a small current is driven. A simultaneous measurement of the resultant voltage drop and/or a time constant associated therewith yields the impedance. Impedance measurement 102 is generated and inputted into the algorithm periodically, e.g., once every 100 ms. It is noted that although successive impedance measurements are generally described herein as being separated by 100 ms, this is by way of illustration and not limitation. For applications in which battery life is not a significant concern, more frequent measurement periods may be used, e.g., once every 10 ms. Alternatively, for some applications, impedance measurements are carried out approximately once every 1-10 seconds, once every 10 seconds to one minute, or once every 1-5 minutes, e.g., once every two minutes.

At a baseline calculation step 106, upon receipt of fundic impedance measurements 102, algorithm 100 uses the impedance measurements to calculate a baseline value of the fundic impedance. Algorithm 100 typically uses a slow-reacting formula for calculating the baseline value, in order to avoid having high frequency noise affect the calculation of the baseline. For example, the algorithm may use the following equation to calculate and update the baseline value:

$$B_t = [B_{t-1}*(N1*N3-1)+X_t]/(N1*N3) \quad \text{(Equation 1)}$$

where $B_t$ is the baseline value at time t (initialized to zero), $B_{t-1}$ is the baseline value at time t−1, N1 is a constant, e.g., 512, $X_t$ is impedance measurement 102 at time t, and N3 is a configurable parameter, typically having a value between about 1 and about 32. For example, N3 may have a value selected from 1, 2, 4, 8, 16, 22, and 32. Higher values of N3 result in slower convergences of $X_t$ to baseline $B_t$. For some applications, the algorithm instead uses Equation 2.1.1 of above-mentioned U.S. Provisional Application 61/051,901. For some applications, the algorithm corrects for baseline drift using techniques described in Section 3.1.1 of the '901 provisional application.

Typically, algorithm 100 applies a high-pass filter to impedance measurement 102, by comparing the measurement to the baseline value, at a high-pass filter step 108. Typically, the algorithm performs this comparison by subtracting the baseline value from impedance measurement 102, resulting in an impedance variance value, i.e., the extent to which the impedance measurement varies from the baseline. Upon initialization of algorithm 100, the algorithm may repeat step 106 for a certain number of periods, so as to obtain a reasonable convergence on the baseline value, prior to performing step 108 for the first time. For some applications, this repetition of step 106 is performed during each cycle through algorithm 100.

Alternatively, algorithm 100 applies a high-pass filter to impedance measurement 102 by using finite and infinite impulse response digital filter design techniques. For example, the resulting filter may take the form of a Butterworth topology or a Chebyshev topology.

Typically, at a low-pass filter step 110, algorithm 100 applies a low-pass IIR filter to the impedance variance value, resulting in a processed impedance value. This low-pass filtering serves to smooth variations in the impedance variance value, and to filter out spurious high and low values. For example, algorithm 100 may use the following equation to perform the low-pass filtering:

$$S_t = [S_{t-1}*(2^{N4}-1)+(X_t-B_t)]/2^{N4} \quad \text{(Equation 2)}$$

wherein $S_t$ is the processed impedance value at time t (initialized to zero), N4 is a configurable parameter, typically having a value between about 1 and about 8, $X_t$ is impedance measurement 102 at time t, and $B_t$ is the last calculated value in step 106, as described above. For example, N4 may have a value selected from 1, 2, 3, 4, 5, 6, 7, and 8. Higher values of N4 tend to reduce false positive indications of ingestion, while lower values tend to reduce false negatives. In general, any of the values 1-8 is suitable. For some applications, the algorithm instead uses Equation 2.1.3 of above-mentioned U.S. Provisional Application 61/051,901.

Alternatively, algorithm 100 applies a low-pass filter to impedance measurement 102 by using finite and infinite impulse response digital filter design techniques. For example, the resulting filter can take the form of a Butterworth topology or a Chebyshev topology.

Algorithm 100 compares the processed impedance value to a configurable fundic increase threshold value, at a fundic impedance check step 112. In an embodiment of the present invention, the fundic increase threshold value is set using techniques described hereinbelow with reference to FIG. 4. The fundic increase threshold value typically is between about 2 and about 80 ohms, such as between about 30 and about 40 ohms. Because the processed impedance value represents a difference between impedance measurement 102 and the baseline value, the fundic increase threshold value is typically expressed as an absolute value (i.e., in ohms), rather than as a percentage change. If algorithm 100 finds that the processed impedance value is less than the fundic increase threshold, the algorithm waits until a new fundic impedance measurement 102 is generated, and repeats the analysis. On the other hand, if algorithm 100 finds at step 112 that the processed impedance value is greater than the fundic increase threshold, the algorithm makes a tentative determination of ingestion by the subject.

For making the tentative determination of ingestion based on antral local sense rate, algorithm 100 has as input an antral local sense measurement 114, as measured by antral local sense electrodes 75. At a rate calculation step 116, algorithm 100 calculates the rate of antral slow waves, such as by using techniques described in above-mentioned PCT Publication WO 06/018851. Algorithm 100 compares the calculated rate to a configurable antral rate decrease threshold value, at an antral sense rate check step 118. The antral rate decrease threshold value typically is between about 2.4 and about 3.33 waves per minute, such as about 2.85 waves per minute. If algorithm 100 finds that the rate is greater than the antral rate decrease threshold, the algorithm waits until a new antral local sense measurement 114 is generated, and repeats the analysis. On the other hand, if algorithm 100 finds at step 118 that the rate is less than the antral rate decrease threshold, the algorithm makes a tentative determination of ingestion by the subject.

Alternatively, and mathematically equivalently, algorithm 100 calculates the interval of the antral slow waves, which is the reciprocal of the rate. Algorithm 100 compares the calculated interval to a configurable antral interval increase threshold value, which is typically between about 18 and about 25 seconds, such as about 21 seconds. If algorithm 100 finds that the interval is less than the antral interval increase threshold, the algorithm waits until a new antral local sense measurement 114 is generated, and repeats the analysis. On the other hand, if algorithm 100 finds at step 118 that the interval is greater than the antral interval increase threshold, the algorithm makes a tentative determination of ingestion by the subject.

In general, the scope of embodiments of the present invention includes mathematically equivalent ways of practicing the embodiments, such as substituting rates for intervals or vice versa, and making appropriate changes to the algorithms.

For some applications, upon making a tentative determination of ingestion of solid food at step 101, in order to determine whether the tentative determination of ingestion is a false positive, algorithm 100 determines the duration of the period during which the processed fundic impedance value rose from baseline to the elevated value exceeding the fundic increase threshold value (as described hereinabove at step 112), and compares the duration to a configurable fundic rise duration threshold value, at a fundic impedance duration check step 120. The fundic rise duration threshold value typically is between about 0.1 and about 10 seconds, or between about 10 and about 60 seconds. If algorithm 100 finds that the duration is less than the fundic rise threshold, the algorithm interprets the tentative determination of ingestion as a false positive, at a false positive determination step 122, and repeats the method of FIG. 3A.

Alternatively, at check step 120 algorithm 100 determines the duration of the period during which the processed fundic impedance value was elevated, i.e., the period beginning when the processed fundic impedance value, when increasing, crossed a fundic impedance threshold value, and concluding when the processed fundic impedance value, when returning towards baseline, again crossed the fundic impedance threshold value. For some applications, the fundic impedance threshold value has the same value as the fundic increase threshold value described hereinabove at step 112, while for other application the fundic impedance threshold value has a value that is different from (i.e., greater or less than) the fundic increase threshold value described hereinabove at step 112. The algorithm compares the duration of elevation with the fundic rise duration threshold value, which, for this technique, is typically between about 0.1 and about 80 seconds, such as between about 2 and about 5 seconds. For some applications, the threshold value is somewhat flexible. For example, the elevated period may conclude when the processed fundic impedance value falls below a value that is greater than the fundic threshold value, such as by a certain number of ohms (e.g., between about two and about 10 ohms), or by a certain percentage of the impedance rise value (e.g., between about 5% and about 30% of the impedance change).

Typically (but not necessarily) in parallel to performing check step 120, algorithm 100 determines whether the food that has been tentatively determined to have been ingested is solid or liquid, at a solid food check step 124, as described hereinbelow with reference to algorithm 200 of FIG. 3B. If algorithm 100 finds that the ingested food was liquid, the algorithm interprets the tentative determination of solid food ingestion as a false positive at false positive determination step 122, and repeats the method of FIG. 3A.

If algorithm 100 finds, at check step 120, that the duration is greater than the fundic rise threshold, and at check step 124, that the ingested food is solid, the algorithm generates an ingestion detection signal, at an ingestion detected step 126. For some applications, algorithm 100 performs only one of the false-positive checks described hereinabove with reference to check steps 120 and 124, rather than both of these checks. For some applications in which the algorithm performs both checks, check step 120 is performed prior to, or simultaneously with, check step 124. Alternatively, for some applications, algorithm 100 interprets the tentative determination of eating as a false positive only if the algorithm finds both (a) at fundic impedance duration check step 120, that the duration is less than the fundic rise threshold, and (b) at solid food check step 124, that the ingested food is liquid. Alternatively, for some applications, algorithm 100 performs neither check step 120 nor check step 124.

As mentioned above, for some applications, algorithm 100 does not include steps 120 through 124, and instead makes a determination of solid ingestion at steps 102 through 118, or steps 102 through 112. For these applications, a final determination of solid ingestion is thus made at step 101, rather than a tentative determination.

FIG. 3B is a flow chart illustrating an algorithm 200 for differentiating between ingestion of solid and liquid food, in accordance with an embodiment of the present invention. As described hereinbelow, algorithm 200 includes several check steps. For some applications, the algorithm performs all of these check steps, while for other applications, the algorithm performs fewer than all of these checks steps, such as only one, two, or three of these check steps, or a combination of certain ones of the conditions. The control unit typically performs the check steps generally in parallel, using software and/or hardware techniques for parallel execution of the algorithm, as known in the art.

At a fundic impedance check step 202, algorithm 200 compares the processed fundic impedance value (determined as described hereinabove at steps 102 through 110 of algorithm 100) to a configurable fundic increase threshold value. The fundic increase threshold value typically is between about 15 and about 80 ohms. If algorithm 200 finds that the processed impedance value is less than the fundic increase threshold, the algorithm tentatively concludes that solid food was ingested, at a solid determination step 204. Otherwise, at a liquid determination step 206, the algorithm tentatively determines that liquid food was ingested, i.e., that the detection of solid food made by algorithm 100 was a false positive.

At a fundic duration check step 208, algorithm 200 determines the duration of the period during which the processed fundic impedance value rose from baseline to the elevated value that exceeds a fundic increase threshold value, and compares the duration to a configurable fundic rise duration threshold value. This calculation of the duration is performed in a similar manner to the calculation described hereinabove at step 120 of algorithm 100. The fundic increase threshold value typically is between about 15 seconds and about 5 minutes. If algorithm 200 finds that the duration is more than the fundic rise threshold, the algorithm tentatively concludes that solid food was ingested, at solid determination step 204. Otherwise, the algorithm tentatively determines that liquid food was ingested at liquid determination step 206.

Alternatively, at check step 208 algorithm 200 determines the duration of the period during which the processed fundic impedance value was elevated, i.e., the period beginning when the processed fundic impedance value, when increasing, crossed a fundic impedance threshold value, and concluding when the processed fundic impedance value, when returning towards baseline, again crossed the fundic impedance threshold value. The algorithm compares the duration of elevation with the fundic rise duration threshold value, which, for this technique, is typically between about 0.1 and about 80 seconds, such as between about 2 and about 5 seconds. For some applications, the threshold value is somewhat flexible. For example, the elevated period may conclude when the processed fundic impedance value falls below a value that is greater than the fundic threshold value, such as by a certain number of ohms (e.g., between about two and about 10 ohms), or by a certain percentage of the impedance rise value (e.g., between about 5% and about 30% of the impedance change).

At an antral impedance check step 210, the algorithm determines a processed antral impedance value, as described below, and compares the processed antral impedance value to a configurable antral increase threshold. Algorithm 200 has as input an antral impedance measurement generated by antral local sense electrodes 75, which are placed on or in the antrum of stomach 20 (FIGS. 1A and 1B). Antral local sense electrodes 75 comprise two or more electrodes through which a small current is driven. A simultaneous measurement of the resultant voltage drop and/or a time constant associated therewith yields the impedance. Algorithm 200 determines the processed antral impedance value by using the antral impedance measurement to calculate a baseline value of the antral impedance, using techniques described hereinabove with reference to baseline calculation step 106. Depending on battery life considerations, step 210 is performed either (a) generally constantly (albeit periodically), even prior to a positive determination at check step 101 of algorithm 100, or (b) only after a positive determination at check step 101. Typically, the algorithm applies one or more filters to the impedance measurement, using techniques described hereinabove with reference to filter steps 108 and 110, in order to derive a processed impedance value. The antral increase threshold value typically is between about 2 and about 30 ohms, such as between about 10 and about 20 ohms, e.g., about 20 ohms. Because the processed impedance value represents a difference between the impedance measurement and the baseline value, the antral increase threshold value is typically expressed as an absolute value (i.e., in ohms), rather than as a percentage change. If algorithm 200 finds that the antral impedance value is more than the antral increase threshold, the algorithm tentatively concludes that liquid food was ingested, at liquid determination step 206. Otherwise, the algorithm tentatively determines that solid food was ingested at solid determination step 204.

At an antral rate check step 212, algorithm 200 determines whether a substantial reduction in an antral local sense rate over a brief period of time, after which the rate returns to baseline, has occurred. For example, the period of time may have a duration of between about 1 and about 3 detected antral waves. Alternatively or additionally, the period of time may have a duration of between about 25 and about 40 seconds. If the local sense interval length is less than an interval length threshold, the algorithm tentatively concludes that solid food was ingested, at solid determination step 204. For example, the rate threshold may be between about 25% and about 75% of the baseline rate. Otherwise, the algorithm tentatively determines that liquid food was ingested at liquid determination step 206.

For some applications, algorithm 200 uses one or more of the techniques described hereinbelow for differentiating between ingestion of predominantly solid and predominantly liquid food.

In an embodiment of the present invention, control unit 90 determines whether ingested food is predominantly solid or predominantly liquid. In order to differentiate between liquids and solids, the control unit analyzes fundic and antral impedances measured by the fundic and antral local sense electrodes 74 and 75, respectively. The control unit determines that ingestion has occurred, using one or more of the ingestion detection techniques described herein and/or in the patents, patent application publications, and patent applications incorporated herein by reference, and/or techniques known in the art. Upon the determination of the ingestion occurrence, the control unit differentiates between ingested liquids and solids using one or more of the following techniques:

- the control unit interprets a change in antral impedance vs. baseline of more than a threshold value as indicating that the ingested food is predominately liquid. For some applications, the threshold value is:
  - (a) dynamically configured to be equal to: (1) a certain percentage of a change in fundic impedance measured during the current detection of ingestion, such as between about 10% and about 100%, or (2) the change in fundic impedance measured during the current detection of ingestion less a constant value, such as between about 0 and about 10 ohms, or between about 10 and about 40 ohms. Apparatus 18 or 18' comprises one or more fundic sensors, configured to be applied to a fundus of the subject, and to generate a fundic signal, and the control unit is configured to determine fundic impedance responsively to the fundic signal;
  - (b) pre-configured to be equal to: (1) a certain percentage of a threshold change in fundic impedance used in the algorithm for detecting ingestion, such as between about 10% and about 100% (for example, techniques may be used for detecting ingestion that are described hereinabove at steps 102 through 112 of algorithm 100, described with reference to FIG. 3A), or (2) the threshold change in fundic impedance used in the algorithm for detecting ingestion less a constant value, such as between about 0 and about 10 ohms, or between about 10 and about 40 ohms (for example, techniques may be used for detecting ingestion that are described hereinabove at steps 102 through 112 of algorithm 100, described with reference to FIG. 3A); or (c) pre-configured to be equal to a constant value, which is typically between about 0 and about 10 ohms, or between about 10 and about 30 ohms.

the control unit compares the fundic impedance value to a configurable fundic increase threshold value. If the control unit finds that the impedance value is less than the fundic increase threshold, the control unit determines that solid food was ingested; otherwise, the control unit determines that liquid food was ingested.

the control unit calculates a duration of the period during which fundic impedance rises from baseline during ingestion of the food. The control unit interprets a duration greater than a first threshold value as indicating that the ingested food is predominantly solid. For example, the first threshold value may be between about 1 and about 5 minutes. A duration less than a second threshold value indicates that the ingested food is predominantly liquid. For example, the second threshold value may be between about 10 seconds and about 5 minutes, e.g., between about 10 and about 60 seconds, or between about 1 and about 5 minutes. A duration between the first and second threshold values is interpreted as being inconclusive regarding the food content.

the control unit calculates an antral local sense rate (i.e., waves per unit time) detected by antral local sense electrodes 75. The control unit interprets a substantial reduction in the rate over a brief period of time, after which the rate returns to baseline, as indicating that the ingested food is predominantly liquid. For example, the period of time may have a duration of between about 1 and about 3 detected antral waves, and the reduction may be at least between about 25% and about 75% of the baseline rate. Alternatively or additionally, the period of time may have a duration of between about 25 and about 40 seconds. A moderate reduction in the rate over a longer period of time typically indicates that the ingested food is predominantly solid. Alternatively or additionally, the control unit calculates the average rate over a brief period of time (e.g., between about 1 and about 6 detected events) and also calculates the standard deviation of the rate. The control unit interprets a low average rate over the averaged period of time as indicating that food (either solid or liquid) has been ingested. If the standard deviation is greater than a threshold value, the control unit determines that the ingested food is predominantly liquid. The inventors hypothesize that the antral local sense rate is correlated with the rate of fundic distension.

In an embodiment of the present invention, check step 112 of algorithm 100, check step 202 of algorithm 200, check step 208 of algorithm 200, and/or check step 210 of algorithm 200 are alternatively calculated using impedance change (fundus or antrum, as appropriate), rather than by comparing the filtered impedance (such as described at step 110 of algorithm 100) to a threshold value. Thus, in this embodiment, high-pass filtering for removing the baseline (such as described at step 108 of algorithm 100) need not be applied. (For using this technique at step 208 of algorithm 200, the start and end points for the duration calculation are typically determined according to the impedance change.)

For some applications, the impedance change is calculated in one of the following ways:

between two defined time points. The time points are typically located at the beginning and end of a sample window that is 5 to 300 seconds long, and the impedance change is calculated by finding the difference between the impedance at the beginning and end of the sample window. Typically, the impedance change is calculated many times during an extended time period, each calculation using the same window duration, but separated in time by a period of up to about half of the duration of the window; or based on a calculated impedance value in two different time windows. The two windows are typically separated by a value that ranges from 0 seconds (i.e., the windows are contiguous) to about 300 seconds. The widths of the windows are typically between about 5 and about 300 seconds, and may be but are not necessarily identical. The calculated impedance value in each window is typically a representative value of the impedance during the corresponding time, and thus may be, for example, the maximum, minimum, or average impedance value in each window. The impedance change is then determined by calculating the difference between the representative values in the two time windows.

In both methods, crossing the threshold of change may be indicative of either solid intake or of liquid intake. For example, if the change is calculated between two time points (or windows) which are close together (for example 10 seconds apart), a crossing of the threshold is indicative of liquid. If the two time points are separated by a larger time interval, a crossing of the threshold is indicative of solid intake, since the duration of rise for liquids is shorter than that for solids. For some applications, the time points or windows and the impedance change threshold are defined differently for each of the check steps.

For some applications, in order to make the tentative determination of ingestion at step 101 of algorithm 100, the algorithm uses techniques other than those described hereinabove with reference to steps 102 through 112 and steps 114 through 118. The algorithm may use one or more of the ingestion detection techniques described in the patents, patent application publications, and patent applications incorporated herein by reference, and/or ingestion detection techniques known in the art, for making the determination of potential ingestion.

In an embodiment of the present invention, control unit 90 uses algorithm 200 of FIG. 3B for independently differentiating between solid and liquid food ingestion, rather than for enhancing the accuracy of solid food ingestion detection.

In an embodiment of the present invention, control unit 90 is configured to provide a "refractory" period, e.g., having a duration of between 0 and 120 minutes (such as in steps of 15 minutes), such as 15 or 90 minutes, following each detection of ingestion (as measured from the conclusion of application of stimulation applied in response to the detection of ingestion), during which a new detection of ingestion is not registered. Such a refractory period is of necessity applied whether the detected ingestion was actual ingestion or a false positive detection of ingestion (i.e., detection of ingestion that did not actually occur). As a result, an occurrence of actual ingestion is sometimes not detected during the refractory period of a false positive detection. The use of the techniques described herein for reducing false positives thus serves to reduce the occurrence of refractory periods induced by false positives, with a concomitant decrease in the likelihood of failing to detect actual ingestion during such false-positive-induced refractory periods. Furthermore, false positives have been demonstrated to have a negative impact on medical outcomes during treatment by electrical stimulation of the stomach (see, for example, p. 119, second paragraph, of the above-cited article by Policker S et al.).

As mentioned hereinabove with reference to FIGS. 1A and 1B, for some applications, control unit 90 is configured to drive current application electrodes 92 to apply an electrical signal to the subject's stomach responsively to device-detected ingestion. For these applications, control unit 90 is typically configured to additionally provide the refractory period throughout the period during which such stimulation is applied, and, optionally, for an additional period after the conclusion of the stimulation period. For example, the control unit may be configured to apply the electrical signal during 45 minutes of a 75-minute stimulation period, and the refractory period may include the 75-minute stimulation period and a 15-minute period immediately thereafter. As a result, a false positive causes a substantial refractory period (90 minutes in this example), during which actual ingestion events cannot be detected. The use of the techniques described herein for reducing false positives thus serves to reduce the occurrence of refractory periods induced by false positives, with a concomitant decrease in the likelihood of failing to detect actual ingestion during such false-positive-induced refractory periods.

In an embodiment of the present invention, upon determining that the ingested food is predominantly liquid (such as using one or more of the techniques described herein, and typically after detecting ingestion by the subject, such as using one or more of the techniques described herein), the control unit determines whether the ingested liquid is high- or low-caloric. If the ingested liquid is low-caloric, the control unit typically does not apply a treatment to the subject, such as electrical stimulation or tightening of a gastric band, as described hereinabove.

For some applications, the control unit determines whether the ingested liquid is high- or low-caloric using one or more of the following techniques (for carrying out these techniques, apparatus 18 or 18' comprises appropriate fundic and/or antral sensors, as described herein):

the control unit interprets a change in antral impedance vs. baseline of more than a threshold value as indicating that the ingested liquid is low-caloric. For some applications, the threshold value is:

(a) dynamically configured to be equal to a certain percentage of a change in fundic impedance measured during the current detection of ingestion, such as between about 5% and about 100%, e.g., between about 10% and about 50%, or between about 50% and about 90%;

(b) pre-configured to be equal to a certain percentage of a threshold change in fundic impedance used in the algorithm for detecting ingestion, such as between about 5% and about 100% (for example, techniques may be used for detecting ingestion that are described hereinabove at steps 102 through 112 of algorithm 100, described with reference to FIG. 3A);

(c) pre-configured to be equal to a certain percentage of a threshold change in antral impedance used in the algorithm for detecting eating (e.g., at step 210 of algorithm 200, described hereinabove with reference to FIG. 3B), such as between about 20% and about 90%, e.g., between about 40% and 70%; or (d) pre-configured to be equal to a constant value, which is typically between about 5 and about 15 ohms, or between about 15 and about 30 ohms.

For some applications, the technique for setting the threshold (e.g., (a)-(d) above) and the parameter(s) of the technique are selected for an individual subject while he is in a clinical setting. Typically, the subject is provided with one or more food intakes (e.g., comprising food having different caloric contents), and the control unit is configured with the technique and parameter(s) of the technique which most accurately correctly determine the caloric content of the intakes.

the control unit interprets a change in fundic impedance vs. baseline of more than a threshold value as indicating that the ingested liquid is low-caloric. For some applications, the threshold value is:

(a) dynamically configured to be equal to: (1) a certain percentage of a change in antral impedance measured during the current detection of ingestion, such as between about 50% and about 200%, or (2) the change in antral impedance measured during the current detection of ingestion plus or minus a constant value, such as between about 0 and about 30 ohms;

(b) pre-configured to be equal to: (1) a certain percentage of a threshold change in fundic impedance used in the algorithm for detecting ingestion, such as between about 50% and about 200%, or (2) the threshold change in fundic impedance used in the algorithm for detecting ingestion less a constant value, such as between about 0 and about 10 ohms, or between about 10 and about 30 ohms;

(c) pre-configured to be equal to: (1) a certain percentage of a threshold change in fundic impedance used in the algorithm for determining that the ingested food is predominantly liquid, such as between about 30% and about 90%, or (2) the threshold change in fundic impedance used in the algorithm for determining that the ingested food is predominantly liquid, plus or minus a constant value, such as between about 5 and about 15 ohms, or between about 15 and about 40 ohms; or (d) pre-configured to be equal to a constant value, which is typically between about 10 and about 25 ohms, or between about 25 and about 60 ohms.

In an embodiment of the present invention, a specific schedule of allowed food ingestion is pre-programmed by the physician into the memory, and ingestion activity analysis block 80 of control unit 90 is continuously operative to detect whether food ingestion is taking place in accordance with the programmed schedule. For some subjects, the schedule may be less strict with respect to drinking liquids or certain types of liquids (e.g., low-caloric liquids), and more strict with respect to ingesting certain types of solid food. When an exception from the schedule is detected, the processor typically actuates a signal generator to generate a signal that discourages the subject from continued ingestion. For example, the signal may include an ingestion-control signal, a satiety inducing signal, a visual, audio, or other cue, tightening of a gastric band or a discomfort-inducing signal.

The timing of the tightening of a gastric band may be selected to achieve a desired goal, including optimal weight loss, blood sugar control, and/or reduction of gastric band complications. The term "timing" in this context means one or more of: (a) the period of time between determination of liquid or solid ingestion and the tightening of a gastric band, (b) the period of time between activating one ingestion control signal and its deactivation, and (c) the timing between activation of an ingestion control signal and its termination (e.g., the period of time between inflating and deflating a gastric band). This timing may vary, for example, in relation to the allowed eating schedule. For example, when the control unit detects ingestion of solid food at a time when such ingestion is not allowed, the control unit may cause the gastric band to be tightened immediately, but when the ingestion of solid food is detected during an allowed ingestion period, the control unit may delay tightening of the gastric band for a period of time to allow sufficient nourishment for the subject. The period may vary between subjects and according to a therapeutic goal. For example, the period may have a duration of between about 10 minutes and about 20 minutes.

For example, techniques may be used that are described in one or more of the following patent applications, all of which are assigned to the assignee of the present application and are incorporated herein by reference:

U.S. Provisional Patent Application 60/259,925, filed Jan. 5, 2001, entitled, "Regulation of eating habits";

PCT Publication WO 02/053093;

PCT Publication WO 05/007232;

U.S. Pat. No. 6,600,953; and/or

PCT Publication WO 06/018851.

Additionally, adjustable band inflation techniques may be used that are described in U.S. Pat. Nos. 5,938,669, 6,460,543, 6,453,907, and/or 6,454,699, and/or in US Patent Application Publication 2001/0011543, relevant portions of all of which are incorporated herein by reference. Alternatively or additionally, other techniques known in the art (e.g., techniques described in one or more of the publications referred to in the Background of the Invention) are utilized for controllably adjusting the circumference of gastric band 32.

In an embodiment of the present invention, if the control unit detects that the ingested food is predominantly liquid, the control unit withholds applying the signal that discourages the subject from continued ingestion. For some applications, the control unit determines whether the liquid is high- or low-caloric, such as by using the techniques described hereinabove. The control unit withholds applying the signal that discourages the subject from continued ingestion only if the liquid is determined to be low-caloric. Alternatively, the control unit does not attempt to determine whether the ingested liquid is high- or low-caloric. The control unit thus withholds applying the signal that discourages the subject from continued ingestion upon detecting that the ingested food is predominantly liquid, without making a further determination regarding the caloric content of the liquid.

Reference is now made to FIG. 4, which is a flow chart illustrating an algorithm 300 for setting a fundic increase threshold value, in accordance with an embodiment of the present invention. The fundic increase threshold value is typically used at fundic impedance check step 112 of algorithm 100, described hereinabove with reference to FIG. 3A. Algorithm 300 is used for individualized calibration of the appropriate fundic increase threshold value for each subject 10. The optimal threshold value varies by individual subject because the range of the measured impedance signal is dependent on the individual subject and the particular electrode implantation characteristics for the subject. Algorithm 300 automates the selection of an optimal threshold for each subject, based on a set of fundic impedance signal data measured during one or more calibration periods.

Typically, algorithm 300 is performed during one or more calibration periods, such as every two to four weeks for several months after implantation of the implantable portions of apparatus 18 or 18' in subject 10, and every few months thereafter. Algorithm 300 is typically performed using a standard computer workstation 320 (FIG. 1A) with an appropriate memory 322, at least one processor 324, communication interfaces, and software for carrying out the functions prescribed by the present invention. This software may be downloaded to the system in electronic form over a network, for example, or it may alternatively be supplied on tangible media, such as CD-ROM. Memory 322 comprises a non-volatile memory, such as one or more hard disk drives, and/or a volatile memory, such as random-access memory (RAM). The interfaces typically comprise an interface 326 for communicating with operator controls 71, either wirelessly or over wires, and/or directly with control unit 90.

Alternatively, in an embodiment of the present invention, algorithm 300 is performed by a control element of apparatus 18 or 18', such as by operator controls 71, by control unit 90, or by operator controls 71 in combination with control unit 90. Performance of the algorithm by the operator controls and/or the control unit may reduce or eliminate the need for follow-up clinical visits for device calibration. Further alternatively, a portion of algorithm 300 is performed by operator control 71 and/or control unit 90, and a portion of the algorithm is performed by workstation 320.

Algorithm 300 begins by receiving a sensed (raw or processed) fundic impedance signal sensed during an initial calibration period using fundic local sense electrodes 74 (FIGS. 1A and 1B), at a fundic impedance signal receipt step 340. For example, the sensed fundic impedance signal may be sensed as described at step 102 of algorithm 100, described hereinabove with reference to FIG. 3A. The sensed fundic impedance signal typically comprises a series of digital values that are stored periodically, e.g., once every 100 ms, in a memory of operator controls 71 and/or control unit 90 during the initial calibration period, which may have a duration, for example, of between one day and several months, e.g., several weeks. Typically, the sensed fundic impedance signal is received via interface 326 of workstation 320 from operator controls 71 or control unit 90, as described above. For some applications, operator controls 71 periodically store a representative sample of the sensed signal, such as once every two minutes, e.g., for a 72-hour period.

Typically, the sensed fundic impedance signal is filtered to generate a filtered fundic impedance signal, at a filtering step 342. For some applications, the filtering is performed as described at steps 106 through 110 of algorithm 100, described hereinabove with reference to FIG. 3A. For example, a baseline value of the fundic impedance may be calculated as described at step 106, a high-pass filter may be applied to the sensed fundic impedance signal as described at step 108, to generate an impedance variance value, and a low-pass filter may be applied to the impedance variance value as described at step 110, to generate the filtered fundic impedance signal. For some applications, all or a portion of this filtering is performed by workstation 320. Alternatively or additionally, all or a portion of this filtering is performed by operator controls 71 and/or control unit 90. In the latter case, the operator controls typically store the filtered or partially filtered signal. In embodiments in which later portions of algorithm 300 are performed by workstation 320, the stored filtered or partially filtered signal is transferred to the workstation.

At an actual ingestion event receipt step 344, an indication is received of actual ingestion events by the subject during the initial calibration period. Typically, the subject or a healthcare worker manually records actual ingestion events throughout the initial calibration period, such as by entering indication of the events into operator controls 71, or making a handwritten record of the events. In embodiments in which workstation 324 performs algorithm 300, in the former case, workstation 324 may receive the indication of the events from operator controls 71 via interface 326. In the latter case, workstation 324 may receive the indication of the events upon the entering of the data of the handwritten record into the workstation or another computer. In embodiments in which operator controls 71 perform at least a portion of algorithm 300, the subject typically enters the indication of the events into the operator controls. In embodiments in which control unit 90 performs at least a portion of algorithm 300, the subject typically enters the indication of the events into operator controls 71, which wirelessly transmit the indication of the events to control unit 90.

Each actual ingestion event includes at least an indication of the commencement time of the event, and, optionally, the completion time of the event, and details regarding the event, such as the type and/or quantity of food ingested, e.g., whether the food is liquid or solid, or other information regarding the food (e.g., caloric content). For some applications, the actual ingestion events include actual solid food ingestion events.

At a candidate thresholds evaluation step 346, a cost function is used to perform an analysis of the filtered fundic impedance signal and the actual ingestion events. Typically, the cost function is used to find each of plurality of cost function values for each of a plurality of respective candidate thresholds. The candidate thresholds typically include all allowable programmable values of device 18 or 18', for example in the range of 8 to 120 ohms in increments of two ohms. To find each of the cost function values, at a detection algorithm step 348 an algorithm is performed that identifies detected ingestion events during the initial calibration period by comparing the filtered fundic impedance signal to the candidate threshold over the initial calibration period. Typically, the algorithm is performed as described at impedance check step 112, described hereinabove with reference to FIG. 3A, using the respective candidate threshold as the fundic increase threshold. At a comparison step 350, the detected ingestion events are compared to the actual ingestion events recorded by the subject or the healthcare worker to find:

a number of the detected ingestion events that represent true positives, i.e., detected ingestion events that correspond to actual ingestion events recorded by the subject or the healthcare worker. For some applications, a true positive is defined as the detection of an ingestion event within a predetermined amount of time (e.g., +/−20 minutes) before or after the occurrence of an actual ingestion event recorded by the subject or the healthcare worker, e.g., by entering the event into operator controls 71;

a number of the detected ingestion events that represent false positives, i.e., detected ingestion events that do not correspond to actual ingestion events recorded by the subject or the healthcare worker. For some applications, a false positive is defined as the detection of an ingestion event in the absence of the occurrence of an actual ingestion event within a predetermined amount of time (e.g., +/−20 minutes) before or after any actual ingestion events; and a number of the actual ingestion events that represent false negatives, i.e., actual ingestion events recorded by the subject or the healthcare worker that do not correspond to detected ingestion events.

(Typically, a number of true negatives is not found, because true negatives are too plentiful, as a result of the sampling frequency, to be useful for analysis.)

The cost function value is calculated for the respective candidate threshold responsively to the number of true positives, the number of false positives, and the number of false negatives, at a cost function value calculation step 352.

Once cost function values have been calculated for all of the candidate thresholds, one of the candidate thresholds is selected as the threshold to be used by apparatus 18 or 18' during future eating detection, responsively to the cost function values, at a select threshold step 354. At a selected threshold storage step 356, the selected threshold is stored in a memory of operator controls 71 and/or control unit 90. In embodiments in which workstation 320 performs step 354, the workstation transmits the selected threshold to the operator controls or control unit for storage. At an eating detection performance step 358, is used for performing eating detection, such as described hereinabove with reference to FIG. 3A. Typically, the threshold is selected responsively to a ranking of the cost function values. For example, the candidate threshold may be selected that is associated with the lowest or nearly lowest (e.g., second or third lowest) one of the cost function values, or with the highest or nearly highest (e.g., second or third highest) one of the cost function values.

For some applications, one or both of the following relationships among true positives (TP), false positives (FP), and false negatives (FN) is used in the cost function at cost function value calculation step 352:

$$\text{Sensitivity} = TP/(TP+FN) \quad \text{(Equation 3)}$$

$$\text{Positive Predictive Value (PPV)} = TP/(TP+FP) \quad \text{(Equation 4)}$$

For some applications, the following cost function is used at cost function value calculation step 352:

$$\text{Cost Function} = \text{Sensitivity} + \text{PPVweighting} * \text{PPV} \quad \text{(Equation 5)}$$

wherein PPVweighting is a constant, typically having a value between 0 and about 10, such as between about 0.7 and about 1.3, e.g., about 1.0. For applications that use Equation 5, the candidate threshold that is associated with the highest or nearly highest one of the cost function values is typically selected at select threshold step 354.

Alternatively, for some applications, such as those with very slow sampling rates, the cost function uses a measure of specificity instead of PPV, such as TN/(TN+FP). For example, the following cost function may be used at cost function value calculation step 352:

$$\text{Cost Function} = \text{Sensitivity} + \text{Spweighting} * \text{Specificity} \quad \text{(Equation 6)}$$

wherein Spweighting is a constant.

Table 1 below shows results of an experiment conducted using apparatus similar to apparatus 18 in 10 human subjects who were obese or both obese and diabetic, in accordance with an embodiment of the present invention. The experiment assessed whether the use of the cost function threshold-setting techniques described hereinabove with reference to FIG. 4 improved the accuracy of detection of ingestion events. Electrodes were implanted on the fundus of each subject, and respective fundic impedance signals were measured during a period having a duration of between about 6 and about 24 hours (depending on each subject's compliance). Actual ingestion events were manually recorded by the subject during the period. The sensed fundic impedance signal was passed through a high-pass filter, by comparing the sensed signal to a baseline value calculated using Equation 1, as described hereinabove with reference to steps 106 and 108 of algorithm 100 of FIG. 3A (N3 was set equal to 16). The resulting impedance variance values were passed through a low-pass filter, as described hereinabove with reference to step 110 of algorithm 100 of FIG. 3A (N4 in Equation 2 was set equal to 4).

Two sets of individualized thresholds were assessed in the experiment: a control set, in which the thresholds were set individually for each subject by a healthcare worker exercising professional judgment, and an experimental set, in which the thresholds were set individually for each subject using the techniques described hereinabove with reference to FIG. 4, in which the PPVweighting constant was set equal to 1.5. The filtered impedance variance values were compared to the two thresholds to detect ingestion events (of solid or liquid food), as described hereinabove with reference to step 112 of algorithm 100 of FIG. 3A. The detected ingestion events were compared to the manually-recorded ingestion events to count true positives (TP), false positives (FP), and false negatives (FN).

TABLE 1

|  | Control Set | | | | Cost Function Set | | | |
| --- | --- | --- | --- | --- | --- | --- | --- | --- |
| Subject # | Threshold | TP | FP | FN | Threshold | TP | FP | FN |
| 1 | 14 | 4 | 3 | 1 | 11 | 5 | 4 | 0 |
| 2 | 22 | 4 | 0 | 0 | 31 | 4 | 0 | 0 |
| 3 | 22 | 5 | 10 | 0 | 33 | 5 | 7 | 0 |
| 4 | 10 | 7 | 4 | 0 | 13 | 7 | 1 | 0 |
| 5 | 24 | 7 | 6 | 0 | 30 | 7 | 2 | 0 |
| 6 | 24 | 6 | 2 | 0 | 20 | 6 | 2 | 0 |
| 7 | 24 | 4 | 3 | 0 | 41 | 3 | 0 | 1 |
| 8 | 16 | 3 | 5 | 0 | 37 | 2 | 0 | 1 |
| 9 | 14 | 3 | 8 | 1 | 47 | 1 | 0 | 3 |
| 10 | 14 | 4 | 3 | 0 | 21 | 4 | 2 | 0 |
| TOTAL | | 47 | 44 | 2 | | 44 | 18 | 5 |

As can be seen in the table, use of the cost function technique resulted in a 59% reduction in total false positives, with only a 6.4% reduction in true positives.

Reference is now made to FIGS. 5A and 5B, which are graphs showing raw measured fundic impedance signals for two of the subjects of the experiment described hereinabove with reference to Table 1, measured in accordance with an embodiment of the present invention. FIG. 5A shows data for Subject 8, and FIG. 5B shows data for Subject 6. Circles 400 and associated first vertical lines 402 indicate ingestion event start times as recorded by the subjects, and second vertical lines 404 following the first vertical lines indicate the conclusion of the ingestion events as recorded by the subjects.

Figure 6A:
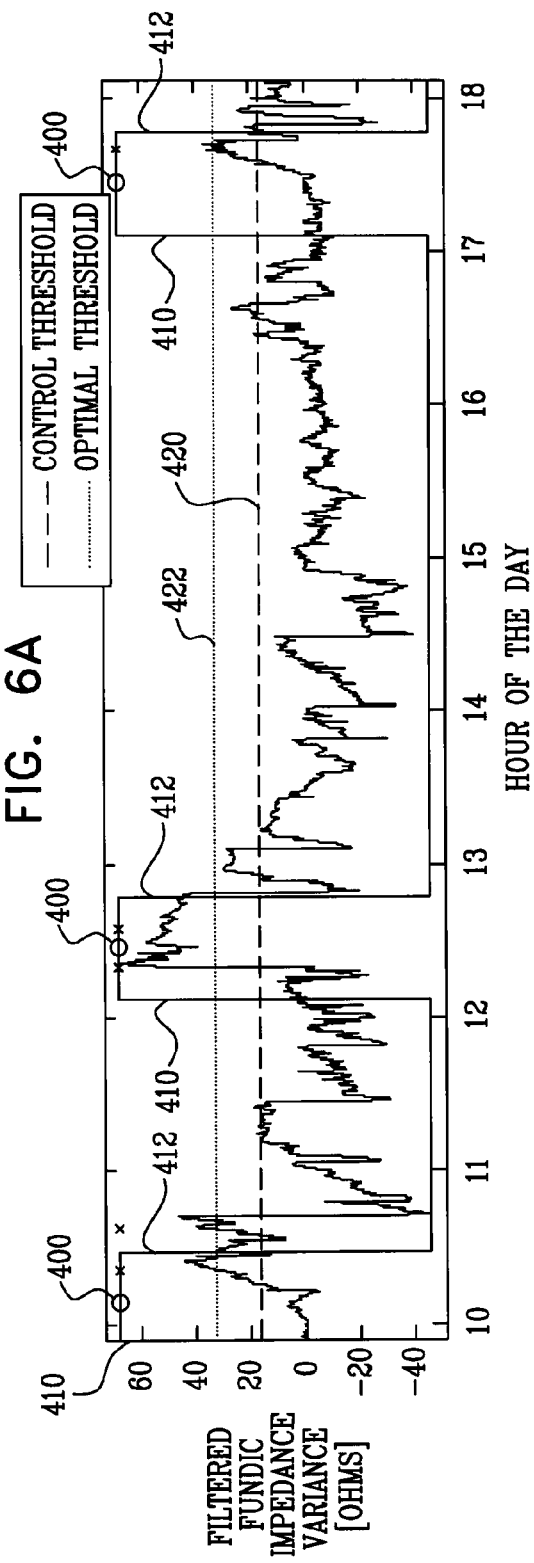
FIGS. 6A and 6B are graphs showing filtered impedance signals for the same two subjects reflected in FIGS. 5A and 5B, respectively, in accordance with an embodiment of the present invention.
Figure 6B:
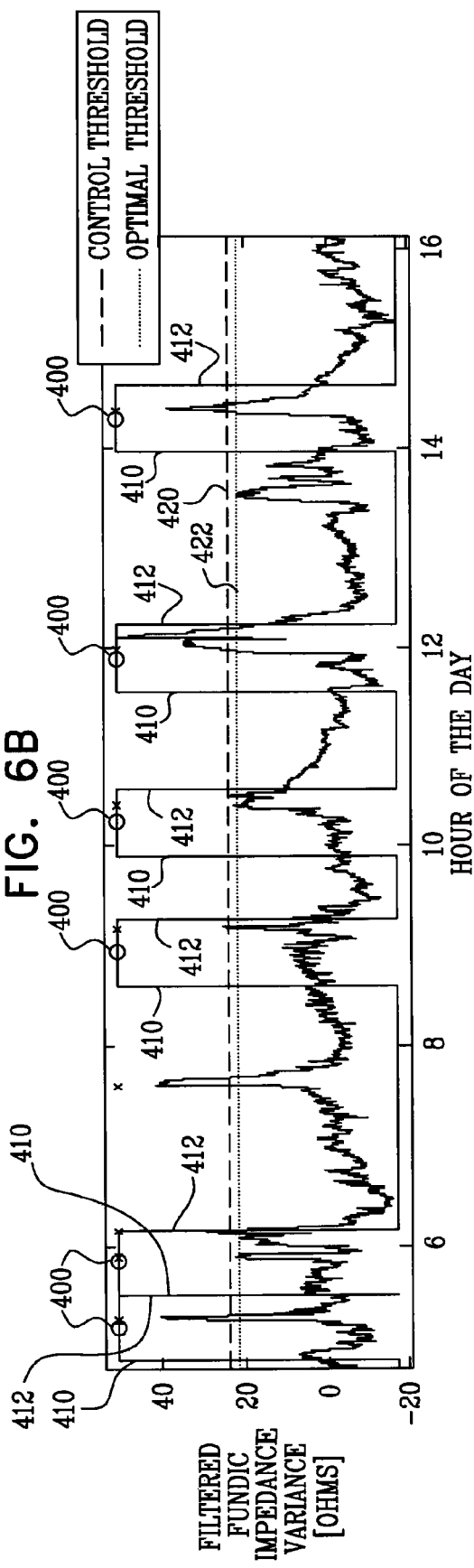

FIGS. 6A and 6B are graphs showing filtered impedance signals for the same two subjects reflected in FIGS. 5A and 5B, respectively, in accordance with an embodiment of the present invention. The raw fundic impedance signals shown in FIGS. 5A and 5B were passed through a high-pass filter, by comparing the raw signals to respective baseline values calculated using Equation 1, as described hereinabove with reference to steps 106 and 108 of algorithm 100 of FIG. 3A (N3 was set equal to 32). The resulting impedance variance values were passed through a low-pass filter, as described hereinabove with reference to step 110 of algorithm 100 of FIG. 3A (N4 in Equation 2 was set equal to 7). (The data shown in FIGS. 6A and 6B is not consistent with the data shown in Table 1 because the values used for N3 in Equation 1 and N4 in Equation 2 to generate the data shown in these figures were different from the values used to generate the data shown in Table 1.)

Circles 400 indicate ingestion event start times as recorded by the subject, and first and second vertical lines 410 and 412 of each set of vertical lines indicate 20 minutes prior to the recorded ingestion start time and 20 minutes after the recorded ingestion start time, respectively. Additionally, the data includes the results of the eating detection algorithm. The "x" symbols indicate eating detection using the optimized thresholds (detected using a refractory period of 15 minutes during which a subsequent ingestion event cannot be detected; for some embodiments, apparatus 18 or 18' instead use a different refractory period, such as 90 minutes). A long-dashed horizontal line 420 indicates the control threshold settings described hereinabove with reference to Table 1. A dotted horizontal line 422 indicates the optimal threshold determined with the cost function described hereinabove with reference to FIG. 4.

The graphs of FIGS. 6A and 6B demonstrate by way of example that the optimized thresholds improve the accuracy of detection of ingestion events. For example, in FIG. 6A, use of the control threshold (line 420) rather than the optimized threshold (line 422) would have resulted in false positives at about 11:15, 13:00, and 16:45. In FIG. 6B, use of the control threshold rather than the optimized threshold would have resulted in a false negative at about 10:30.

In some embodiments of the present invention, techniques described herein are practiced in combination with techniques described in the above-mentioned article by Policker S et al.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Provisional Patent Application 60/259,925, filed Jan. 5, 2001, entitled, "Regulation of eating habits";

PCT Patent Application PCT/IL02/00007, filed Jan. 3, 2002, entitled, "Regulation of eating habits";

PCT Patent Application PCT/IL00/00132, filed Mar. 5, 2000, entitled, "Blood Glucose Level Control," and U.S. patent application Ser. No. 09/914,889 in the national stage thereof, which issued as U.S. Pat. No. 7,006,871, and U.S. patent application Ser. No. 11/318,845, which is a division thereof;

PCT Patent Application PCTIL00/00566, filed Sep. 13, 2000, entitled, "Blood Glucose Level Control," and U.S. patent application Ser. No. 10/237,263, filed Sep. 5, 2002, which is a continuation-in-part thereof;

PCT Patent Application PCT/IL03/000736, filed Sep. 4, 2003, entitled, "Blood Glucose Level Control," and U.S. patent application Ser. No. 10/526,708 in the national stage thereof, and U.S. patent application Ser. No. 10/804,560, filed Mar. 18, 2004, which is a continuation-in-part thereof;

PCT Patent Application PCT/IL04/000797, filed Sep. 5, 2004, entitled, "Blood Glucose Level Control," and U.S. patent application Ser. No. 10/570,576 in the national stage thereof;

PCT Patent Application PCT/IL04/000664, filed Jul. 21, 2004, entitled, "Gastrointestinal methods and apparatus for use in treating disorders and controlling blood sugar"; U.S. patent application Ser. No. 09/734,358, filed Dec. 21, 2000, entitled, "Acute and chronic electrical signal therapy for obesity," which issued as U.S. Pat. No. 6,600,953;

PCT Patent Application PCT/IL05/000904, filed Aug. 18, 2005, entitled, "Monitoring, analysis, and regulation of eating habits," which published as WO 06/018851, and U.S. patent application Ser. No. 11/573,722 in the national stage thereof;

U.S. Provisional Patent Application 60/602,550, filed Aug. 18, 2004, entitled, "Monitoring, analysis, and regulation of eating habits"; PCT Patent Application PCT/IL2007/000052 to Levi et al., filed Jan. 14, 2007, entitled, "Electrode assemblies, tools, and methods for gastric wall implantation," which published as PCT Publication WO 07/080,595;

PCT Patent Application PCT/IL2006/000198 to Ben-Haim, filed Feb. 15, 2006, entitled, "Charger with data transfer capabilities," and U.S. patent application Ser. No. 11/816,574 in the national stage thereof;

PCT Patent Application PCT/IL2005/000316 to Harel et al., filed Mar. 18, 2005, entitled, "Gastrointestinal methods and apparatus for use in treating disorders and controlling blood sugar," and U.S. patent application Ser. No. 10/599,015 in the national stage thereof;

PCT Patent Application PCT/IL2004/000550 to Ben-Haim et al., filed Jun. 20, 2004, entitled, "Gastrointestinal methods and apparatus for use in treating disorders," which published as PCT Publication WO 04/112563, and U.S. patent application Ser. No. 10/561,491 in the national stage thereof;

PCT Patent Application PCT/IL2006/000204, filed Feb. 16, 2006, entitled, "Non-immediate Effects of Therapy," and U.S. patent application Ser. No. 11/884,389 in the national stage thereof;

PCT Patent Application PCT/US05/044557, filed Dec. 9, 2005, entitled, "Protein Activity Modification," and U.S. patent application Ser. No. 11/792,811 in the national stage thereof; PCT Patent Application PCT/US06/17281, filed May 4, 2006, entitled, "Protein Activity Modification," and U.S. patent application Ser. No. 11/919,491 in the national stage thereof, and U.S. patent application Ser. No. 11/802,685, filed May 25, 2007, which is a continuation-in-part thereof;

PCT Patent Application PCT/US2006/010911 to Policker et al., filed Mar. 24, 2006, entitled, "Wireless leads for gastrointestinal tract applications," which published as PCT Publication WO 06/102626, and a U.S. patent application filed Sep. 24, 2007 in the national stage thereof;

PCT Patent Application PCT/IL2006/000644 to Policker et al., filed Jun. 4, 2006, entitled, "GI lead implantation," which published as PCT Publication WO 06/129321;

U.S. Provisional Patent Application 60/916,919, filed May 9, 2007, entitled, "Analysis and regulation of food intake."

U.S. Provisional Application 61/051,901, filed May 9, 2008, entitled, "Optimization of filters and parameters for eating detection"; and/or PCT Patent Application PCT/IL08/000,646, filed May 11, 2008, entitled, "Analysis and regulation of food intake."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
receiving, by a processor, a fundic impedance signal of a subject sensed during an initial calibration period using at least one implantable fundic sensor of an eating detection device;
receiving, by the processor, an indication of actual ingestion events of the subject during the initial calibration period;
performing, by the processor, an analysis of the fundic impedance signal and the actual ingestion events, using a cost function to find each of a plurality of cost function values for each of respective candidate thresholds by:
identifying, using an eating detection algorithm, detected ingestion events during the initial calibration period by comparing the fundic impedance signal to the candidate threshold over the initial calibration period,
comparing the detected ingestion events to the actual ingestion events to find a number of the detected ingestion events that represent true positives, a number of the detected ingestion events that represent false positives, and a number of the actual ingestion events that represent false negatives, and
calculating the cost function value responsively to a measure of sensitivity of the eating detection algorithm and a measure of positive predictive value of the eating detection algorithm, wherein the sensitivity equals the quotient of (a) the number of the true positives divided by (b) a sum of the number of the true positives and the number of the false negatives, and wherein the positive predictive value equals the quotient of (a) the number of the true positives divided by (b) a sum of the number of the true positives and the number of the false positives;
setting, by the processor, a threshold by selecting one of the candidate thresholds as the threshold responsive to the cost function values, the crossing of which threshold by the fundic impedance signal is indicative of ingestion; and
storing, by the processor, the threshold in a memory of the eating detection device.

2. The method according to claim 1,
wherein receiving the fundic impedance signal comprises:
receiving, by the processor, a sensed fundic impedance signal of the subject sensed during the initial calibration period using the at least one implantable fundic sensor; and,
filtering, by the processor, the sensed fundic impedance signal to generate a filtered fundic impedance signal, and
wherein performing the analysis comprises performing the analysis of the filtered fundic impedance signal and the actual ingestion events.

3. The method according to claim 2, wherein receiving the sensed fondle impedance signal comprises receiving a representative sample of a raw fondle impedance signal, and wherein filtering comprises filtering the representative sample of the raw fundic impedance signal to generate the filtered fundic impedance signal.

4. The method according to claim 1, wherein receiving the fundic impedance signal comprises receiving a filtered fondle impedance signal from the eating detection device, and wherein performing the analysis comprises performing the analysis of the filtered fundic impedance signal and the actual ingestion events.

5. The method according to claim 1, wherein performing the analysis and setting the threshold by the processor comprise performing the analysis and setting the threshold by a processor of the eating detection device.

6. The method according to claim 1, wherein performing the analysis and setting the threshold by the processor comprise performing the analysis and setting the threshold by a processor of a computer workstation separate from the eating detection device, and wherein storing the threshold in the memory of the eating detection device comprises transmitting, by the processor of the workstation, the threshold to the eating detection device.

7. The method according to claim 1, wherein selecting the one of the candidate thresholds comprises selecting the one of the candidate thresholds responsively to a ranking of the cost function values.

8. The method according to claim 1, wherein calculating the cost function comprises calculating a sum of the measure of sensitivity and a product of the measure of positive predictive value and a weighting factor.

9. The method according to claim 8, wherein the weighting factor is between 0.7 and 1.3.

10. The method according to claim 1, further comprising, during a treatment period after the initial calibration period:
sensing, using the at least one fundic sensor of the eating detection device, a treatment sensed fundic impedance signal;
filtering, by the eating detection device, the treatment sensed fundic impedance signal to generate a treatment filtered fundic impedance signal; and
identifying, by the eating detection device, a treatment period ingestion event by comparing the treatment filtered fundic impedance signal to the selected one of the thresholds stored in the memory of the eating detection device.

11. The method according to claim 10, further comprising, responsively to identifying the treatment period ingestion event, applying a treatment to the subject by the eating detection device.

12. The method according to claim 1, wherein the actual ingestion events are actual solid food ingestion events, and wherein receiving the indication of the actual ingestion events comprises receiving the indication of the actual solid food ingestion events by the subject during the initial calibration period.

13. The method according to claim 1, wherein receiving the fundic impedance signal comprises receiving a set of filtered fundic impedance increase vs. baseline values, and wherein setting the threshold comprises setting a fundic impedance increase vs. baseline threshold.

14. Apparatus for use with an eating detection device having a memory and at least one implantable fundic sensor, the apparatus comprising:
an interface, configured to communicate with the eating detecting device; and
a processor, configured:
to receive, via the interface, a fundic impedance signal of a subject sensed during an initial calibration period using the at least one implantable fundic sensor of the eating detection device;
to receive an indication of actual ingestion events of the subject during the initial calibration period;
to perform an analysis of the fundic impedance signal and the actual ingestion events, using a cost function to find each of a plurality of cost function values for each of respective candidate thresholds by:
identifying, using an eating detection algorithm, detected ingestion events during the initial calibration period by comparing the fundic impedance signal to the candidate threshold over the initial calibration period,
comparing the detected ingestion events to the actual ingestion events to find a number of the detected ingestion events that represent true positives, as number of the detected ingestion events that represent false positives, and a number of the actual ingestion events that represent false negatives, and
calculating the cost function value responsively to a measure of sensitivity of the eating detection algorithm and a measure of positive predictive value of the eating detection algorithm, wherein the sensitivity equals the quotient of (a) the number of the true positives divided by (b) is sum of the number of the true positives and the number of the false negatives, and wherein the positive predictive value equals the quotient of (a) the number of the true positives divided by (b) a sum of the number of the true positives and the number of the false positives;

to set a threshold, by selecting one of the candidate thresholds a the threshold responsively to the cost function values, the crossing of which threshold by the fundic impedance signal is indicative of ingestion; and
to store, via the interlace, the threshold in the memory of the eating detection device.

15. The apparatus according to claim 14, wherein the processor is configured to filter the fundic impedance signal to generate a filtered fundic impedance signal, and to perform the analysis of the filtered fundic impedance signal and the actual ingestion events.

16. The apparatus according to claim 14, wherein the fundic impedance signal includes a filtered fundic impedance signal, and wherein the processor is configured to receive the filtered fundic impedance signal from the eating detection device, via the interface, and to perform the analysis of the filtered fundic impedance signal and the actual ingestion events.

17. The apparatus according to claim 14, wherein the processor is configured to select the one of the candidate thresholds responsively to a ranking of the cost function values.

18. The apparatus according to claim 14, wherein the processor is configured to calculate the cost function by calculating a sum of the measure of sensitivity and a product of the measure of positive predictive value and a weighting factor.

19. The apparatus according to claim 14, wherein the actual ingestion events are actual solid food ingestion events, and wherein the processor is configured to receive the indication of the actual solid food ingestion events by the subject during the initial calibration.

20. Apparatus comprising:
one or more implantable fundic sensors, configured to be applied to a fundus of a subject, and to generate a fundic, impedance signal; and
a control element, which comprises a memory, and which is configured to:
receive the fundic impedance signal sensed during an initial calibration period,
receive an indication of actual ingestion events of the subject during the initial calibration period,
perform an analysis of the fundic impedance signal and the actual ingestion events, using a cost function to find each of a plurality of cost function values for each of respective candidate thresholds by:
identifying, using an eating detection algorithm, detected ingestion events during the initial calibration period by comparing the fundic impedance signal to the candidate threshold over the initial calibration period,
comparing the detected ingestion events to the actual ingestion events to find a number of the detected ingestion events that represent true positives, a number of the detected ingestion events that represent false positives, and a number of the actual ingestion events that represent false negatives, and
calculating the cost function value responsively to a measure of sensitivity of the eating detection algorithm and as measure of positive predictive value of the eating detection algorithm, wherein the sensitivity equals the quotient of (a) the number of the true: positives divided by (b) a sum of the number of the true positives and the number of the false negatives, and wherein the positive predictive value equals the quotient of (a) the number of the true positives divided by (b) a sum of the number of the true positives and the number of the false positives, set a threshold by selecting one of the candidate thresholds as the threshold responsively to the cost function values, the crossing of which threshold by the fundic impedance signal is indicative of ingestion, and store the threshold in the memory.

21. The apparatus according to claim 20, wherein the control element is configured to filter the fluidic impedance signal to generate a filtered fundic impedance signal, and perform the analysis of the filtered fondle impedance signal and the actual ingestion events.

22. The apparatus according to claim 20, wherein the control element is configured to selecting the one of the candidate thresholds responsively to a ranking of the cost function values.

23. The apparatus according to claim 20, wherein the control element is configured to calculate the cost function by calculating a sum of the measure of sensitivity and a product of the measure of positive predictive value and a weighting factor.

24. The apparatus according to claim 20, wherein the control element is configured to during a treatment period after the initial calibration period, receive, from the at least one fundic sensor, a treatment sensed fundic impedance signal, filter the treatment sensed fundic impedance signal to generate a treatment filtered fundic impedance signal, and identify a treatment period ingestion event by comparing the treatment filtered fundic impedance signal to the selected one of the thresholds stored in the memory of the eating detection device.

25. The apparatus according to claim 24, further comprising an implantable treatment unit, wherein the control element is configured to drive the implantable treatment unit to apply a treatment to the subject, responsively to identifying the treatment period ingestion event.

26. The apparatus according to claim 20, wherein the actual ingestion events are actual solid food ingestion events, and wherein the control element is configured to receive the indication of the actual solid food ingestion events by the subject during the initial calibration period.

27. A computer software product for use with an eating detection device having a memory and at least one implantable fundic sensor, the product comprising a tangible computer-readable medium in which program instructions are stored, which instructions, when read by a computer, cause the computer to receive a fundic impedance signal of a subject sensed during an initial calibration period using the at least one implantable fundic sensor of the eating detection device; to receive an indication of actual ingestion events of the subject during the initial calibration period; to perform an analysis of the fundic impedance signal and the actual ingestion events, using a cost function to find each of a plurality of cost function values for each of respective candidate thresholds by: (a) identifying, using an eating detection algorithm, detected ingestion events during the initial calibration period by comparing the fundic impedance signal to the candidate threshold over the initial calibration period, (b) comparing the detected ingestion events to the actual ingestion events to find a number of the detected ingestion events that represent true positives, a number of the detected ingestion events that represent false positives, and a number of the actual ingestion events that represent false negatives, and (c) calculating the cost function value responsively to a measure of sensitivity of the eating detection algorithm and a measure of positive predictive value of the eating detection algorithm, wherein the sensitivity equals the quotient of (i) the number of the true positives divided by (ii) a sum of the number of the true positives and the number of the false negatives, and wherein the positive predictive value equals the quotient of (i) the number of the true positives divided by (ii) a sum of the number of the true positives and the number of the false positives; to set a threshold by selecting one of the candidate thresholds as the threshold responsively to the cost function values, the crossing of which threshold by the fundic impedance signal is indicative of ingestion; and to store the threshold in the memory of the eating detection device.

28. The computer software product according to claim 27, wherein the instructions, when read by the computer, cause the computer to select the one of the candidate thresholds responsively to a ranking of the cost function values.

* * * * *

UNITED STATES PATENT AND TRADEMARK OFFICE
CERTIFICATE OF CORRECTION

PATENT NO. : 8,423,130 B2  
APPLICATION NO. : 12/256819  
DATED : April 16, 2013  
INVENTOR(S) : James Thrower et al.

Page 1 of 1

It is certified that error appears in the above-identified patent and that said Letters Patent is hereby corrected as shown below:

In the Claims:

Column 30, Claim 2, line 6, "and," should read -- and --.

Column 30, Claim 3, each of lines 2 and 3, "fondle" should read -- fundic --.

Column 30, Claim 4, line 2, "fondle" should read -- fundic --.

Column 31, Claim 14, line 24, "as" should read -- a --, and line 33, "is" should read -- a --.

Column 32, Claim 14, line 40, "a" should read -- as --, and line 43, "interlace" should read -- interface --.

Column 32, Claim 19, line 5, "calibration" should read -- calibration period --.

Column 32, Claim 20, line 3, "fundic," should read -- fundic --, line 28, "as" should read -- a --, and line 31, "true:" should read -- true --.

Column 33, Claim 21, line 2, "fluidic" should read -- fundic -- and line 4, "fondle" should read -- fundic --.

Signed and Sealed this  
Eighteenth Day of June, 2013

Teresa Stanek Rea  
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,423,130 B2 | Page 1 of 1 |
| APPLICATION NO. | : 12/256819 | |
| DATED | : April 16, 2013 | |
| INVENTOR(S) | : James Thrower et al. | |

It is certified that error appears in the above-identified patent and that said Letters Patent is hereby corrected as shown below:

In the Claims:

Column 30, line 27 (Claim 2, line 6) "and," should read -- and --.

Column 30, lines 35 and 36 (Claim 3, each of lines 2 and 3) "fondle" should read -- fundic --.

Column 30, line 42 (Claim 4, line 2) "fondle" should read -- fundic --.

Column 31, line 53 (Claim 14, line 24) "as" should read -- a --.

Column 31, line 62 (Claim 14, line 33) "is" should read -- a --.

Column 32, line 2 (Claim 14, line 40) "a" should read -- as --.

Column 32, line 5 (Claim 14, line 43) "interlace" should read -- interface --.

Column 32, line 31 (Claim 19, line 5) "calibration" should read -- calibration period --.

Column 32, line 34 (Claim 20, line 3) "fundic," should read -- fundic --.

Column 32, line 59 (Claim 20, line 28) "as" should read -- a --.

Column 32, line 62 (Claim 20, line 31) "true:" should read -- true --.

Column 33, line 7 (Claim 21, line 2) "fluidic" should read -- fundic --.

Column 33, line 9 (Claim 21, line 4) "fondle" should read -- fundic --.

This certificate supersedes the Certificate of Correction issued June 18, 2013.

Signed and Sealed this
Sixteenth Day of July, 2013

Teresa Stanek Rea
*Acting Director of the United States Patent and Trademark Office*